US007061523B2

United States Patent
Fujita et al.

(10) Patent No.: US 7,061,523 B2
(45) Date of Patent: Jun. 13, 2006

(54) CAPSULE TYPE MEDICAL DEVICE

(75) Inventors: Manabu Fujita, Hino (JP); Masatoshi Homan, Hino (JP)

(73) Assignee: Olympus Corporation, Tokyo (JP)

( * ) Notice: Subject to any disclaimer, the term of this patent is extended or adjusted under 35 U.S.C. 154(b) by 675 days.

(21) Appl. No.: 10/215,063

(22) Filed: Aug. 8, 2002

(65) Prior Publication Data

US 2003/0085994 A1 May 8, 2003

(30) Foreign Application Priority Data

Nov. 6, 2001 (JP) .............................. 2001-341101

(51) Int. Cl.
*H04N 7/18* (2006.01)

(52) U.S. Cl. ........................................ 348/77; 600/309

(58) Field of Classification Search .................. 348/76, 348/77; 604/890.1; 442/111; 351/206; 250/208.1; 600/109, 309, 300

See application file for complete search history.

(56) References Cited

U.S. PATENT DOCUMENTS 4,278,077 A * 7/1981 Mizumoto ................. 600/109
4,722,860 A * 2/1988 Doljack et al. ............. 442/111
5,395,366 A * 3/1995 D'Andrea et al. ........ 604/890.1
5,604,531 A * 2/1997 Iddan et al. .................. 348/76
6,030,080 A * 2/2000 Ohman ....................... 351/206
6,497,656 B1 * 12/2002 Evans et al. ................ 600/300
6,667,468 B1 * 12/2003 Kurosawa et al. ....... 250/208.1
6,800,060 B1 * 10/2004 Marshall ..................... 600/309

FOREIGN PATENT DOCUMENTS

JP       7-111985     5/1995
JP      2001-46357     2/2001

\* cited by examiner

*Primary Examiner*—Gims Philippe
(74) *Attorney, Agent, or Firm*—Scully, Scott, Murphy & Presser, P.C.

(57) ABSTRACT

Signals are sent by radio waves from a single or multiple antennas provided in an external unit located outside of a living body to a capsule inserted into a living body to obtain living body information. The signals are received by the antenna on the capsule side and the radio wave strength data is obtained. Based on the radio wave strength data, living body information is sent from the capsule side to the external unit by using a transmission power suitable for the transmission. The radio wave strength data is sent to the external unit side, and the external unit side receives living body information by selecting and using an antenna, which can receive data with the highest radio wave strength.

43 Claims, 15 Drawing Sheets

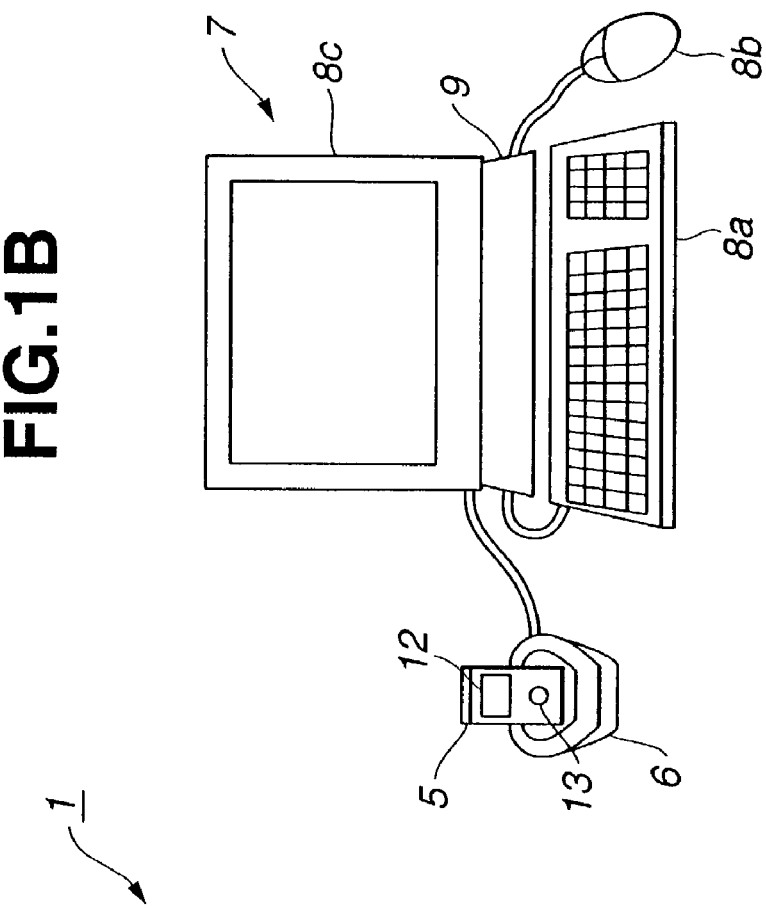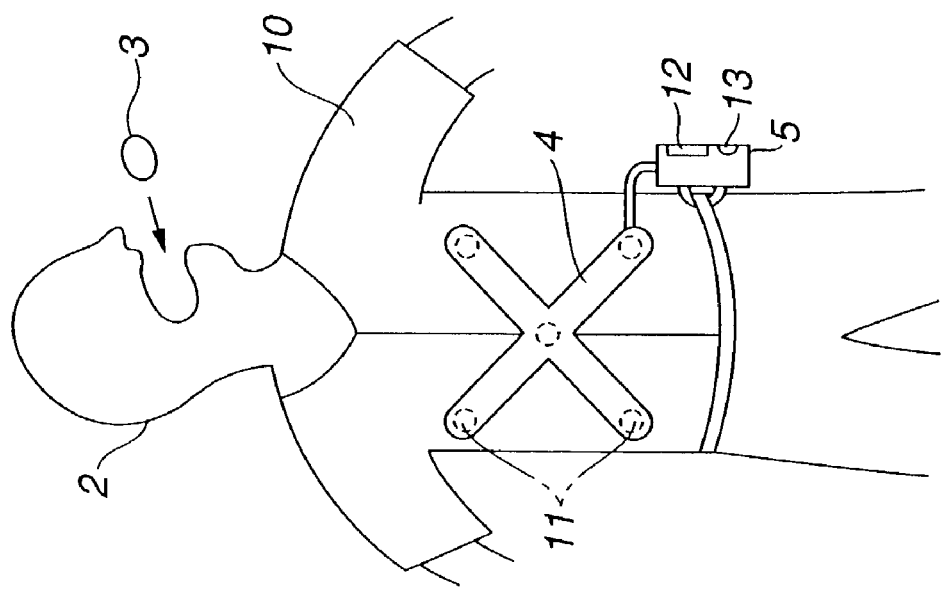

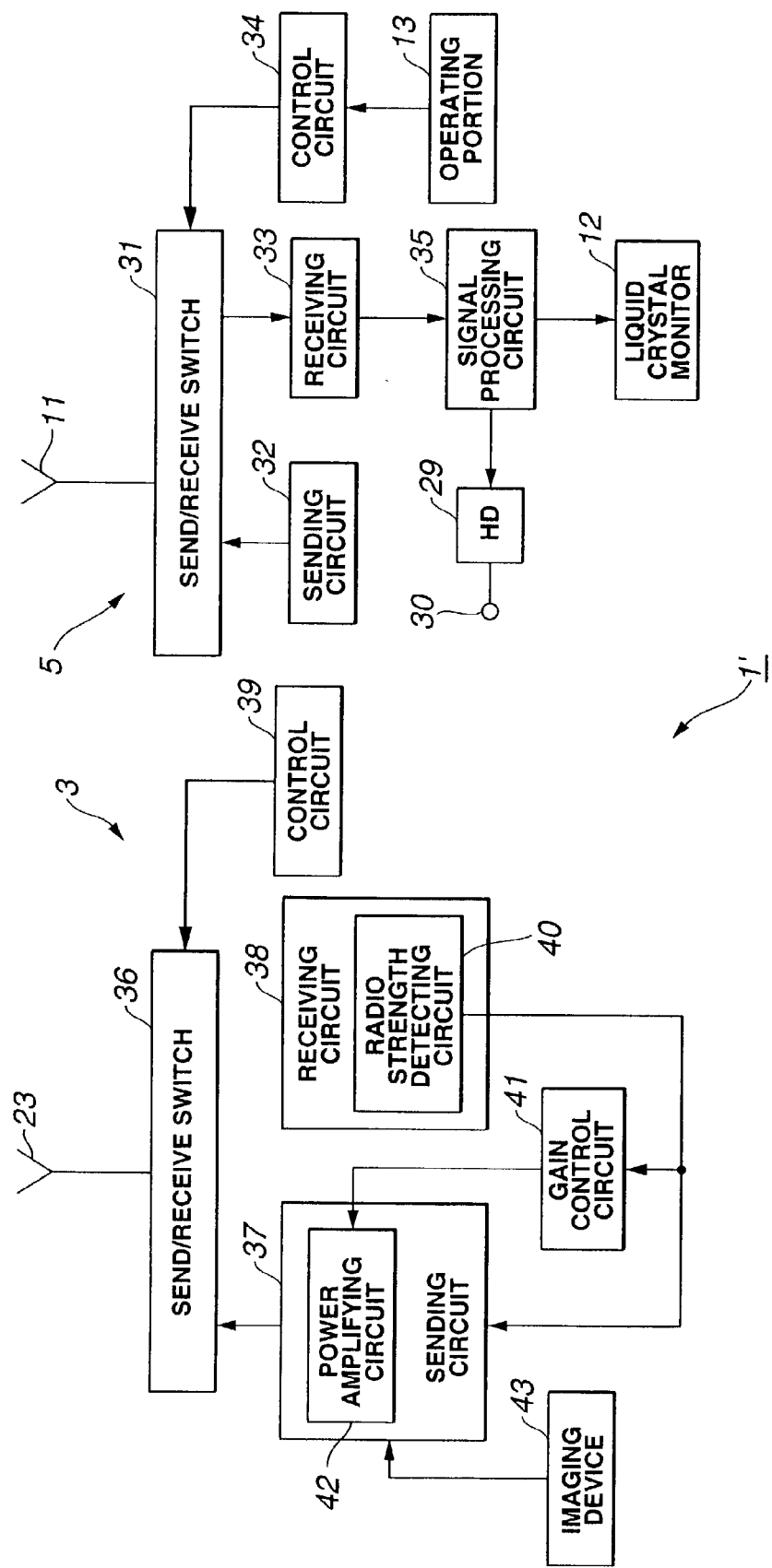

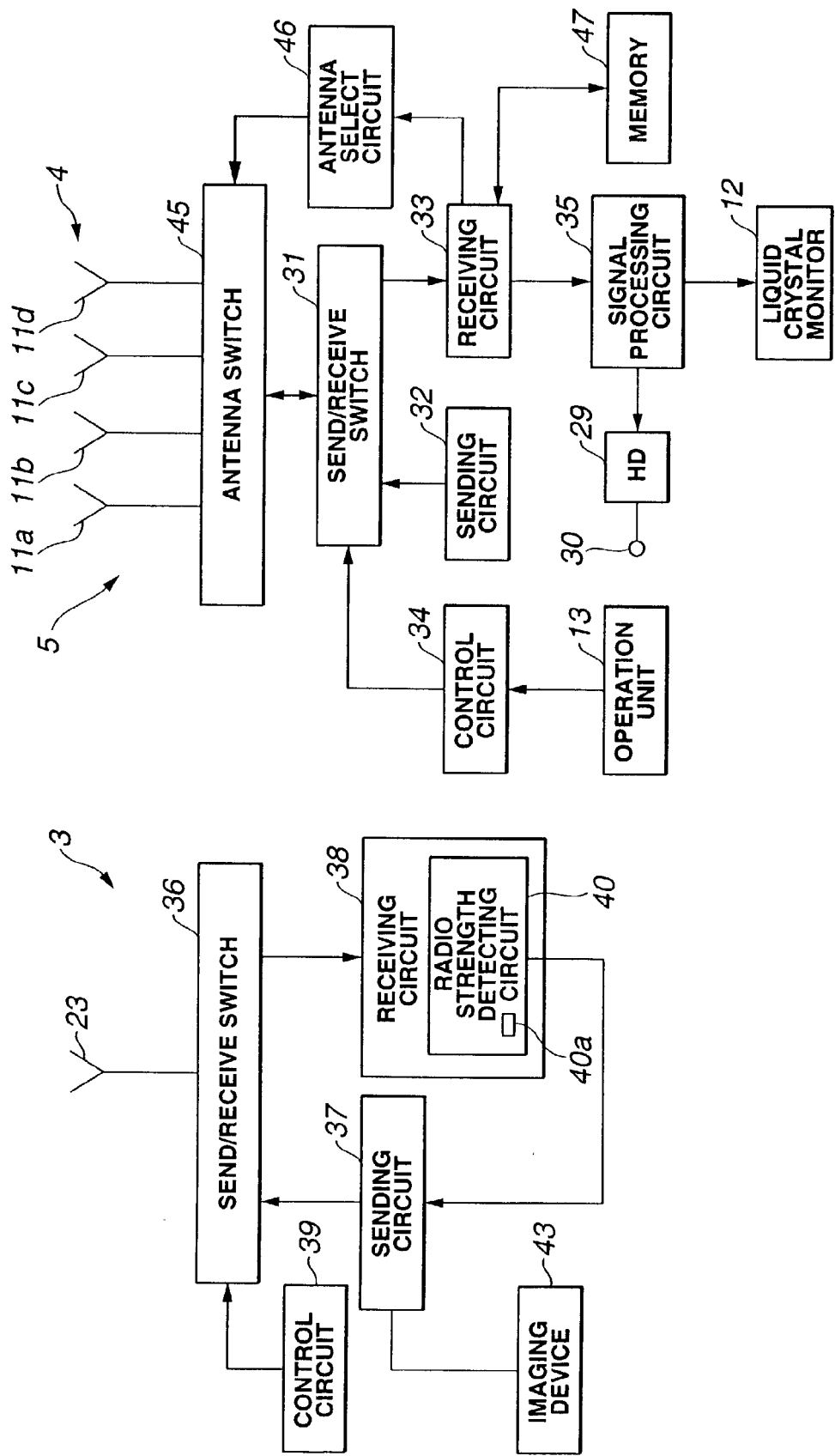

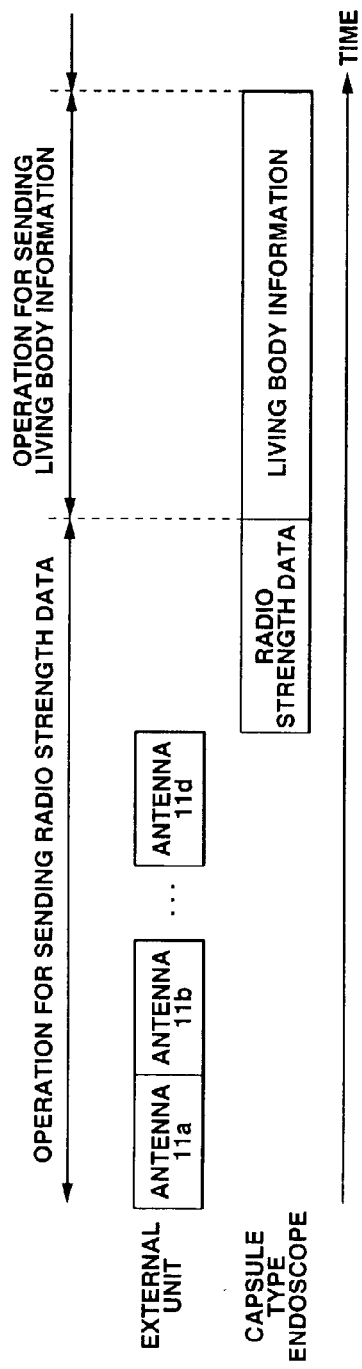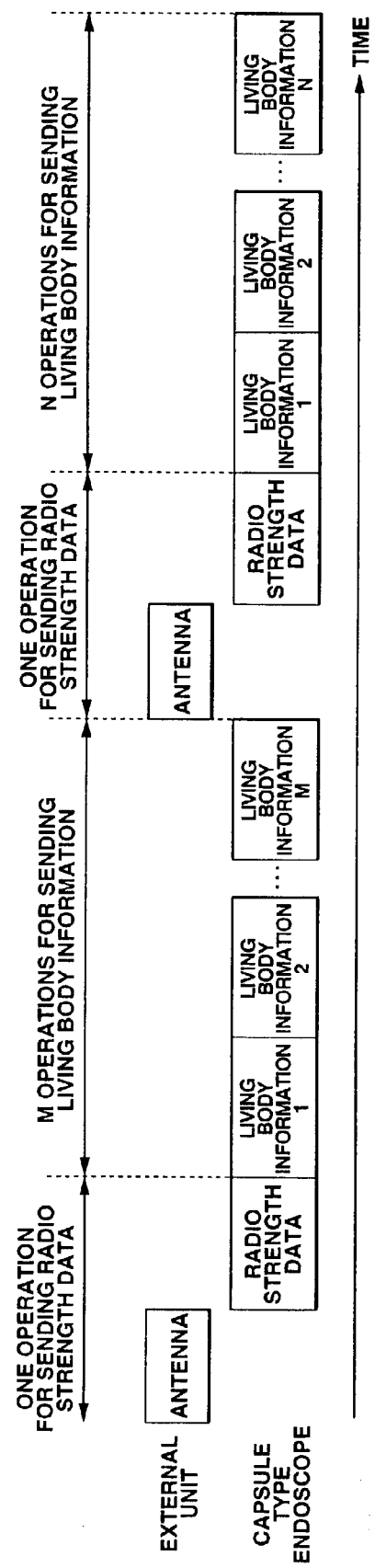

CAPSULE TYPE MEDICAL DEVICE

This application claims benefit of Japanese Application No. 2001-341101 filed on Nov. 6, 2001, the contents of which are incorporated by this reference.

BACKGROUND OF THE INVENTION

1. Field of the Invention

The present invention relates to a capsule type medical device including a swallowable capsule and an external unit of receiving living body information sent from the capsule.

2. Description of the Related Art

Recently, a capsule type device has been proposed whereby a capsule body in capsule form is inserted into a body cavity for examination.

For example, according to a first technology of the related art, disclosed in Japanese Unexamined Patent Application Publication No. 7-111985, a spherical capsule, which is divided into two, is used to communicate living body information to an external device via a communication unit.

However, the example of the related art does not consider the proper transmission of living body information from the capsule side to the external device side.

Thus, the capsule side has to send living body information with higher transmission power as much as possible so that the external device side can receive the information surely. In this case, electric energy in a battery built in the capsule is consumed largely, thus shortening the capsule usable time.

It may be considered that the transmission power is reduced in order to increase the lifetime of the battery. In this case, however, the information cannot be received by the external device side fully.

A second technology of the related art disclosed in the Japanese Unexamined Patent Application Publication No. 2001-46357 is a system for receiving signals from the capsule side at a plurality of antennas in the external unit side in order to obtain living body information including position information.

Furthermore, a third technology of the related art disclosed in the U.S. Pat. No. 5,604,531 is a system for receiving signals corresponding to an image sent from the capsule to the external device side by a plurality of antennas in order to select an antenna, which has the largest signal strength.

In this case, a plurality of antenna are used and an antenna, which has the largest signal strength, is selected so that the signals from the capsule can be received more surely than the case using one antenna. However, like the case of the first technology of the related art, it is not arranged so as to set the proper transmission power on the capsule side.

SUMMARY OF THE INVENTION

Accordingly, it is an object of the present invention to provide a capsule type medical device, which allows the detection for setting proper transmission power and the like.

It is another object of the present invention to provide a capsule type medical device, which can send information by using proper transmission power.

There is provided a capsule type medical device, including a capsule inserted into a living body, having a living body information detecting device for obtaining living body information, an external unit located outside of the living body, a first sending and receiving circuit provided in the external unit for signal sending and receiving, a first antenna connected to the first sending and receiving circuit, a second sending and receiving circuit provided in the capsule for signal sending and receiving, a second antenna connected to the second sending and receiving circuit, and a radio wave strength detecting circuit for detecting radio wave strength when a signal sent from the first sending and receiving circuit side through the first antenna is received by the second sending and receiving circuit through the second antenna. Thus, when information of the radio wave strength detected by the radio wave strength detecting circuit and living body information are sent, proper transmission power can be set.

In addition, a transmission power value may be controlled by the second sending and receiving circuit based on the detected output from the radio wave strength detecting circuit. Thus, a proper transmission output value can be set for transmitting living body information.

BRIEF DESCRIPTION OF THE DRAWINGS

FIGS. 1A to 8B relate to a first embodiment of the present invention;

FIG. 1A is a diagram showing the configuration of a capsule type endoscope device according to the first embodiment of the present invention;

FIG. 1B is a diagram showing the configuration of an external device such as an external terminal device;

FIG. 2 is a sectional view showing the internal configuration of the capsule type endoscope;

FIG. 3 is a block diagram showing the configuration of a main portion of a capsule type endoscope device when the external unit side has one antenna;

FIG. 4 is a block diagram showing the configuration of a main portion of a capsule type endoscope device when the external unit side has multiple antennas;

FIG. 5 is an explanatory diagram showing an operation for sending radio wave strength data and living body information between the external unit and the capsule type endoscope;

FIG. 6 is an explanatory diagram showing an operation performed when the number of times for transmitting radio wave strength data and living body information is changed;

FIG. 7 is an explanatory diagram showing the detection of the position of the capsule type endoscope by using multiple antennas;

FIG. 8B is a diagram showing the configuration of a capsule type endoscope in the variation example;

FIG. 9 is a block diagram showing the configuration of a main portion of a capsule type medical device according to the second embodiment of the present invention;

FIG. 10 is a block diagram showing the configuration of a main portion of a capsule type medical device in a variation example;

FIGS. 11 to 17B relate to a third embodiment of the present invention;

FIG. 11 is a block diagram showing the configuration of a main portion of a capsule type medical device according to the third embodiment of the present invention;

FIG. 12 is a block diagram showing the configuration of a main portion of an external unit in a first variation example;

FIG. 13 is an explanatory diagram for an operation in the case in FIG. 12;

FIG. 14 is a schematic diagram of a second variation example;

FIG. 15 is a diagram showing an example where a third variation example is used as a whole;

FIG. 16 is a diagram showing a place near the external unit in a shield jacket;

FIG. 17B is a diagram showing a case when the key is inserted into the keyhole;

FIG. 18 is a sectional view showing the configuration of a capsule type medical device according to a fourth embodiment of the present invention;

FIG. 19 is a sectional view showing the configuration of a capsule type medical device according to a first variation example;

FIG. 20 is a sectional view showing the configuration of a capsule type medical device according to a second variation example; and FIG. 21 is a partial cutaway view of the configuration of a capsule type medical device of a third variation example.

DESCRIPTION OF THE PREFERRED EMBODIMENTS

First Embodiment

Figure 2:
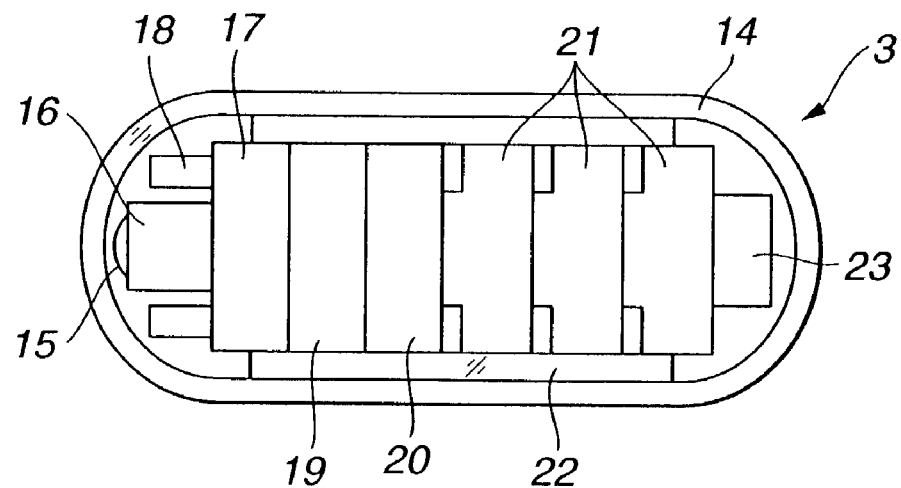

A first embodiment of the present invention will be described with reference to FIGS. 1A to 8B.

As shown in FIG. 1A, a capsule type endoscope device 1 according to the first embodiment of the present invention includes a capsule type endoscope 3 for detecting the inside of a body cavity, which is swallowed by a patient 2, and an external unit 5, which is located outside of the patient 2 and is connected to an antenna unit 4 which receives by wireless means image information captured by the capsule type endoscope 3.

As shown in FIG. 1B, the external unit 5 is attached to a cradle 6 and is electrically connected to a terminal device 7 such as a personal computer. The terminal device 7 can capture into a terminal body 9 an image stored in the external unit 5 by manipulating an input/manipulation device such as a keyboard 8a and a mouse 8b and can display the captured image on a monitor portion 8c.

As shown in FIG. 1A, when the patient 2 swallows the capsule type endoscope 3 for endoscopic examination, the patient 2 wears a shirt 10, to which an antenna unit 4 is attached. Multiple antennas 11 are mounted on the antenna unit 4. Picking up an image is performed by the capsule type endoscope 3. Then, the antenna unit 4 receives signals sent by an antenna 23 (FIG. 2), which is built in the capsule type endoscope 3. Then, the captured image can be stored in the external unit 5, which is connected to the antenna unit 4. The external unit 5 is removably attached, by using a hook, to a belt of the patient 2, for example.

The external unit 5 is, for example, in box shape, and has, on the front, a liquid crystal monitor 12 for image display and an operating portion 13 for performing instruction operations and so on.

As shown in FIG. 2, the capsule type endoscope 3 is in cylinder form having both ends are rounded in substantially hemisphere form. That is, the capsule type endoscope 3 is covered by a capsule-shape, clear external member 14 in a watertight manner. An objective lens 15 for forming images is mounted on a lens frame 16 on a center part of one end portion, which is an image capturing side, within the clear external member 14. A CMOS image-pickup element 17, which is an image pickup element, is arranged on the image forming position.

A white-color LED 18 is arranged as a lighting system around the objective lens 15. Provided at the back of the CMOS image-pickup element 17 are a processing circuit 19, a communication processing circuit 20, and button-type batteries 21. They are arranged within a clear cylinder member 22 within the external member 14. The processing circuit 19 emits light to drive the white-color LED 18 and generates image signals from image-picked-up signals by the CMOS image-pickup element 17. The communication processing circuit 20 sends image signals and/or receives signals to or from the external unit 5. The button type battery 21 supplies power supply to these circuits 19 and 20. An antenna 23 connected to the communication processing circuit 20 are located at the back end of the button type battery 21, that is, inside of the other hemisphere. The antenna 23 sends/receives radio waves.

In the capsule type endoscope device 1 according to this embodiment, as described below, the external unit 5 sequentially sends signals having certain strength from the sending circuit via each of the antennas 11 of the antenna unit 4. On the other hand, the capsule-type endoscope 3 receives signals in the receiving circuit included in the communication processing circuit 20 via the antenna 23. The received radio wave strength information is modulated in digital again and is sent from the capsule-type endoscope 3 side to the external unit 5 side.

Thus, it is set in the external unit 5 so that one of the antennas 11, which is suitable for receiving signals from the capsule-type endoscope 3, is used. Then, image signals sent from the capsule-type endoscope 3 actually can be received certainly.

When there is provided a single antenna 11 in the antenna unit 4, the transmission power is adjusted on the capsule-type endoscope 3 side.

Before describing a case where there are provided multiple antennas 11, as shown in FIG. 1A, a case of a capsule-type endoscope device having only one antenna 11 will be described.

FIG. 3 shows the configuration of a main portion of a capsule-type endoscope device 1' having only one antenna 11.

In the external unit 5, the antenna 11 is connected to a sending circuit 32 and a receiving circuit 33 through the send/receive switch 31. The switching of the send/receive switch 31 is controlled by a control circuit 34. An operating portion 13 is connected to the control circuit 34. The receiving circuit 33 is connected to a hard disk 29 for storing image data, the liquid crystal monitor 12 for displaying images and so on, via a signal processing circuit 35.

Then, when an instruction for starting transmission is input by manipulating the operating portion 13, the control circuit 34 connects the send/receive switch 31 to the sending circuit 32 side. Then, signals for starting transmission from the sending circuit 32 at a predetermined level are sent from the antenna 11. After the transmission, the control circuit 34 connects the send/receive switch 31 to the receiving circuit 33 side and sends received image signals to the signal processing circuit 35. Then, the signals are processed and the image data is stored in the hard disk 29 and/or the transmitted image is displayed by the liquid crystal monitor 12. The hard disk 29 is connected to the connector 30 via an interface, not shown, so that image data, which is living body information, stored in the hard disk 29 can be read out.

In the capsule-type endoscope 3 side, the antenna 23 is connected to a sending circuit 37 and a receiving circuit 38 via a send/receive switch 36. The switching of send/receive switch 36 is controlled by the control circuit 39.

When signals corresponding to an initial state, for example, are sent from the external unit 5 side over radio waves, the antenna 23 is connected to the receiving circuit 38. Then, the radio wave strength of the signals received by the receiving circuit 38 is detected by a radio wave strength detecting circuit 40 within the receiving circuit 38.

The digital data for the detected radio wave strength is output to a gain control circuit 41. Based on the digital data, the gain control circuit 41 adjusts an amount of power amplification by a power amplifying circuit provided within the sending circuit 37 in order to set proper transmission power, which can be received by the external unit 5 side.

Signals imaged by the CMOS image-pickup element 17 and being processed by the processing circuit 19 are input to the sending circuit 37. The sending circuit 37 sends signals captured by the CMOS image-pickup element 17. The CMOS image-pickup element 17 and the processing circuit 19 are indicated by an image pickup device 43 in FIG. 3.

In this embodiment, as upstream processing for sending image signals captured from the capsule-type endoscope 3, a signal for starting the transmission from the external unit 5 side is sent to the capsule-type endoscope 3. The capsule-type endoscope 3 receives the signal. According to this embodiment, there is provided a radio wave strength detecting circuit 40 for detecting the radio wave strength of the signal.

It is arranged such that, after using the detected radio wave strength for setting transmission power in the sending circuit 37, image signals, which are actually captured, are sent.

For example, when the detected radio wave strength is high, it is set to a state that the gain of the power amplification by the power amplifying circuit 42 is suppressed. On the other hand, when the detected radio wave strength is low, it is set to a state that the gain of the power amplification is increased for sure receiving. When the detected radio wave strength is very low and there is a higher possibility for mis-receiving, the transmission is stopped.

Therefore, the power is not wasted due to the unnecessary increase in the transmission power, and the capsule-type endoscope 3 can send image signals by setting a transmission power value, which is suitable for receiving the signal at the external unit 5 side. For that, the waste of the electric energy in the battery 21 can be prevented, allowing the increase in operationable time as a result.

Since the capsule type endoscope 3 can move within the body of the patient 2. A signal for detecting radio wave strength can be sent from the external unit 5 side at both initialization time and the other time in the same manner. Then, the capsule-type endoscope 3 updates the transmission power based on the signal. Thus, when the capsule-type endoscope 3 moves within the body of the patient 2, proper transmission power can be set, preventing the waste of energy in the battery 21 and keeping the proper send/receive condition as a result.

Next, a case where multiple antennas 11 are used in the antenna unit 4, shown in FIG. 1A, will be described with reference to FIG. 4.

Other than the configuration in FIG. 3, in the external unit 5, the send/receive switch 31 may be connected to multiple antennas 11a to 11d, which constitute the antenna unit 4, via the antenna switch 45. (Reference numerals a to d are added for clearer description rather than using "multiple antennas 11".)

The antenna switch 45 switches antennas 11i (i=a to d) selected by an antenna select circuit 46 and connects the selected antenna to the send/receive switch 31. In the meantime, the antenna select circuit 46 is controlled by the output from the receiving circuit 33.

A memory 47 for temporally stores received data is connected to the receiving circuit 33.

When an instruction for starting transmission is input from the operating portion 13, a signal for starting the transmission is sent through the send/receive switch 31 and via antennas 11a, 11b, . . . and 11d, which are sequentially selected by the antenna select circuit 46. Then, the send/receive switch 31 is connected to the receiving circuit 33 side and receives the signals sent by the capsule-type endoscope 3 via the antennas 11a, 11b, . . . , and 11d, which are sequentially selected by the antenna select circuit 46.

Here, if the capsule-type endoscope 3 receives signals sent via each of antennas 11i, the radio wave strength is detected by the radio wave strength detecting circuit 40 in the receiving circuit 38, as shown in FIG. 3. Then, the radio wave strength data is modulated in digital and is sent to the sending circuit 37. Then, signals corresponding to the radio wave strength information are sent from the antenna 23 to the external unit 5 side. The radio wave strength data may be stored in the memory 40a, which may be provided in the radio wave strength detecting circuit 40 until the signals are completely sent via all of the antennas 11a, 11b, . . . , and 11d.

Then, the external unit 5 receives the signals by using the receiving circuit 33 via the sequentially switched antennas 11a, 11b, . . . and 11d. The receiving circuit 33 sends a control signal to the antenna select circuit 46 so as to select an antenna 11i, which is determined to have the highest radio wave strength based on the received signals. The antenna select circuit 46 is set so as to receive signals sent from the capsule-type endoscope 3 via the antenna 11i.

On the other hand, in the configuration in FIG. 3, the capsule-type endoscope 3 has a configuration without the gain control circuit 41 in the sending circuit 37. Therefore, the sending circuit 37 is arranged not to control the power amplification by using the gain control circuit 41 (the power amplification is controlled in the later-described embodiment).

In the capsule-type endoscope 3 is set such that the send/receive switch 36 is connected to the receiving circuit 38 under the control of the control circuit 39. The receiving circuit 38 receives signals sequentially sent from the external unit 5 via the antenna 11i, which is sequentially switched. Then, the radio wave strength detecting circuit 40 detects the radio wave strength of the received signals and sends the digital data for the radio wave strength to the sending circuit 37. The digital data is sent from the sending circuit 37 to the external unit 5 via the antenna 23.

The external unit 5 side receives the digital data for the radio wave strength, and receives the subsequent signals by using the antenna 11 whose radio wave strength is determined as the highest.

The example of operations along a time axis in this case is shown in FIG. 5. The horizontal axis in FIG. 5 indicates a lapse of time.

First of all, an operation for sending radio wave strength data is performed. In this case, the external unit 5 sequentially sends signals with certain strength by using antenna 11a, 11b, . . . , and 11d. The capsule-type endoscope 3 receives respective signals and detects the respective radio wave strength. Once radio wave strength data is received for all of antennas 11a, 11b, . . . , and 11d, the radio wave strength data is modulated and is sent from the antenna 23 to the external unit 5 side.

The external unit 5 receives the radio wave strength data by switching antennas 11a, 11b, . . . , and 11d, for example, and obtains information on the antenna 11i, which has the highest radio wave strength. Then, it is set to use the antenna 11i, through which the highest radio wave strength data can be obtained.

After that, an operation for sending living body information is performed. Under this state, the external unit 5 side is set to use the antenna 11i, from which the highest radio wave strength data can be received, and the capsule-type endoscope 3 sends, as living body information, information on a captured image.

Since the capsule-type endoscope 3 moves within a body, the antenna 11i, through which the highest radio wave strength data can be received, must be changed. Therefore, the operation for sending radio wave strength data and the operation for sending living body information, shown in FIG. 5, are repeated at intervals of proper period of time.

Thus, even when the capsule-type endoscope 3 moves within the body, living body information can be obtained by using the antenna 11i, which can detect the highest radio wave in that state based on the movement.

In reality, since a movement speed of the capsule-type endoscope 3 within the body is very low, the same radio wave strength data is sent if one operation for sending radio wave strength data is performed for one operation for sending living body information. Then, the power consumption may be wasteful.

In order to avoid this, M, N or multiple times of operations for sending living body information may be performed when one operation for sending radio wave strength data is performed, as shown in FIG. 6. Furthermore, it may be arranged such that the ratio of the operation for sending radio wave strength data and the operation for sending living body information can be changed easily. The antennas indicated in the operations for sending radio wave strength data in FIG. 6 summarize antennas 11a to 11d in FIG. 5.

Furthermore, according to this embodiment, the radio wave strength data sent via multiple antennas 11a, 11b, . . . , and 11d is used as position information for locating a position where living body information is obtained.

Figure 7:
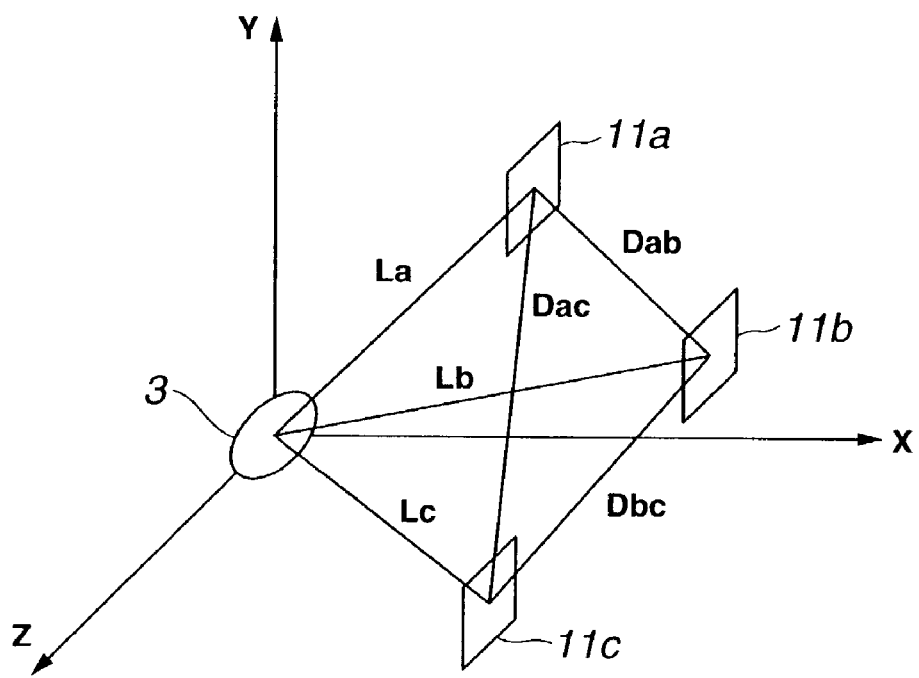

FIG. 7 shows an explanatory diagram where position information for the capsule-type endoscope 3 is obtained via multiple antennas. Here, this is a case where the capsule-type endoscope 3 is set at the origin of the three-dimensional coordinates X, Y and Z.

The multiple, that is, three antennas 11a, 11b and 11c here, for simple description, included in the antenna unit 4 are located at respective known places. The distances between these antennas are also known.

FIG. 7 includes a distance Dab between the antennas 11a and 11b, a distance Dbc between the antennas 11b and 11c, and a distance Dac between the antennas 11a and 11c.

On the other hand, the signal strength of signals, which are emitted by radio wave from an antenna 11j (j=a, b or c) and are received by the antenna 23 in the capsule-type endoscope 3 is a function of a distance Li. More specifically, an amount of radio wave reduction depends on the distance Li.

Therefore, radio wave strength data, which is sent from the capsule-type endoscope 3 by using the receiving circuit 33 is temporally stored in the memory 47 of the external unit 5. Then, the distance Li between the external unit 5 and (the antenna 23 of) the capsule-type endoscope 3 is calculated based on the data. Then, the calculated distance Li is sent to the signal processing circuit 35 side by, for example, adding it to living body information.

When living body information, that is image information here, is displayed on the liquid crystal monitor 12, the position information may be displayed. When the position information is displayed, a schematic shape of a living body may be displayed in order to indicate a position where the image information is obtained. Thus, the position where the image information is obtained within a living cavity is known, which allows much easier diagnoses from the image information having the position information than from the image information without position information.

Figure 8A:
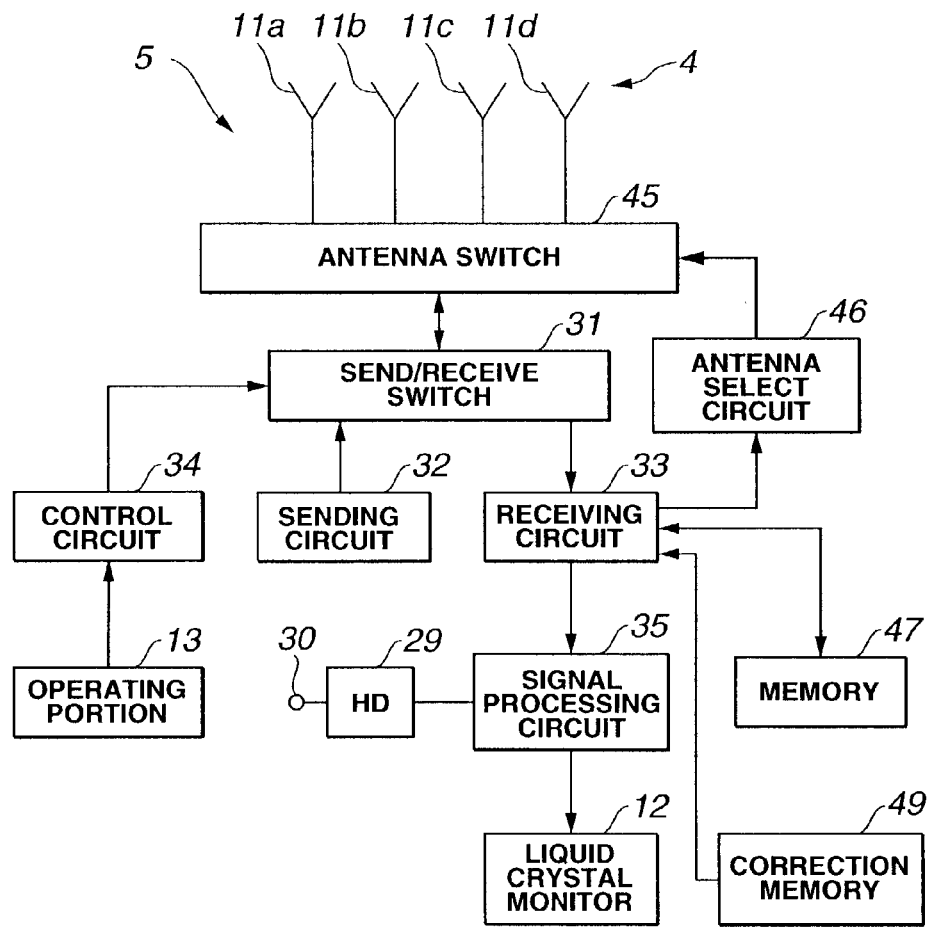
FIG. 8A is a block diagram showing the configuration of a main portion of an external unit in a variation example.

As shown in a variation example in FIG. 8A, a correction memory 49 may be further provided in the external unit 5 shown in FIG. 4. The correction memory 49 stores a correction value for correcting an antenna gain error for multiple antennas 11a to 11d and an error in loss component due to the length of the cable therebetween when radio wave strength data detected in the capsule-type endoscope 3 is received.

A receiving circuit 33 corrects radio wave strength data stored in the memory 47 by using a correction value stored in the correction memory 49. Thus, the radio wave strength data is corrected in order to obtain radio wave strength data with higher precision. The radio wave strength data can be used for antenna selection and a position can be detected with higher precision than the case where position information is calculated from the radio wave strength data.

According to this embodiment, means is provided for detecting radio wave strength when radio transmission is performed between the capsule-type endoscope 3 side and the external unit 5 side.

Therefore, based on the information on the detected radio wave strength, the capsule-type endoscope 3 can send signals by using proper transmission power. Furthermore, the external unit 5 side can receive signals by using an antenna among the multiple antennas 11, which has the highest radio wave strength.

This embodiment is described by using a CMOS image-pickup element as an image pickup element or an image pickup device. However, the image pickup element in this embodiment is not limited thereto. Three kinds on image pickup elements may be used as described below in variation examples. Next, a first variation will be described with reference to FIG. 8B.

Figure 8B:
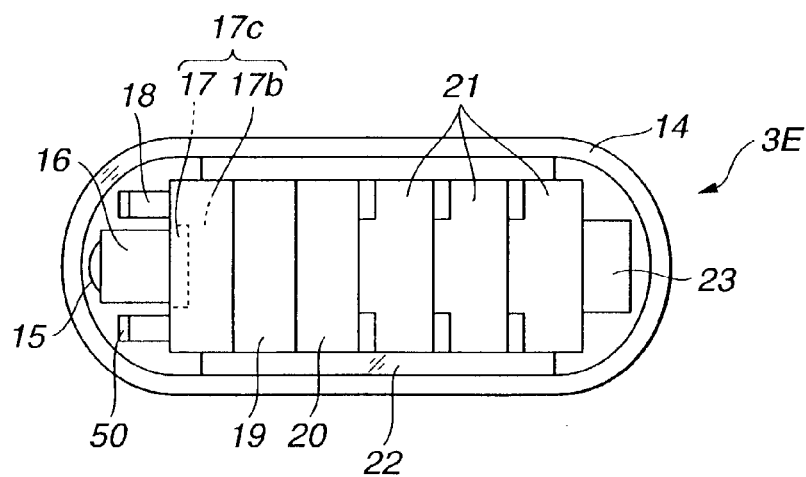

FIG. 8B shows a capsule-type endoscope 3E using an artificial retina. In the capsule-type endoscope 3 in FIG. 3, the capsule-type endoscope 3E uses a so-called artificial retina LSI 17c, which is a system LSI having in one chip the CMOS image-pickup element 17 and the image processing circuit 17b for image processing, instead on the CMOS image-pickup element 17.

The chip performs processing for image detection and processing for image feature extraction at the same time and has the same functions as those of the human retina. A usual CCD or CMOS image sensor only detects images, and feature processing and authentication processing are performed by using an external image processor. However, these kinds of processing are performed by the artificial retina LSI 17c chip, which can achieve the simple and compact circuit. Furthermore, there are merits such as fast processing, driving with a single power supply and driving with low power consumption.

Therefore, it is suitable for a disposable, capsule-type endoscope. By using this feature, a disposable endoscope (softscope or hardscope) and a low-price endoscope can be achieved. Therefore, each of these endoscopes can use the image sensor (artificial retina LSI 17c) as the usual videoscope, of course.

In addition, there are excellent features as below:

(a) Built-in image profile extraction, white-balance, edge emphasis, brightness adjustment, gamma correction functions and A/D conversion functions;

(b) High sensitivity and high image quality;

(c) Small sized package; and (d) Optional built-in noise reducing circuit (correlation dual sampling circuit).

There are many types of sensors such as QCIF (QSIF) size, 160×144 size, CIF (SIF) size, VGA type, SVGA type and XGA type. For the radio wave communication type of capsule endoscope like this embodiment, a smaller one such as QCIF (QSIF) size, 160×144 size and CIF (SIF) size is especially suitable in view of easy swallowing, radio transmission speed and power consumption.

Second variation uses a threshold value modulation type image sensor (VMIS), which is the next generation image sensor having both merits of the CCD and the CMOS image-pickup element. This sensor is completely different in configuration from the CMOS sensor of the related art having a receiving portion including three to five transistors and photodiodes. This is an image sensor having a configuration using a technology whereby a threshold value of a MOS transistor is modulated with a charge generated by light receiving and the change in threshold value is output as an image signal.

The feature of the image sensor is that a CCD with high image quality and high integrity of the CMOS sensor, driving with low voltage and low power consumption can be achieved at the same time.

Therefore, the disposable type capsule endoscope is suitable. By using the feature, the disposable-type endoscope (softscope or hardscope) and the low-price endoscope can be achieved. Then, this kind of image sensor (VMIS) can be used for these kinds of endoscope and usual video scopes. In addition, it has excellent features as follows:

(a) The simple configuration having one transistor for each image sensor;

(b) Excellent photoelectric characteristics such as high sensitivity and high dynamic range; and (c) Higher density and lower price due to the manufacturing in the CMOS process.

There are many types of sensors such as QCIF (QSIF) size, CIF (SIF) size, VGA type, SVGA type and XGA type. For the radio wave communication type of capsule endoscope like the present invention, a smaller one such as QCIF (QSIF) size and CIF (SIF) size is especially suitable in view of easy swallowing, radio transmission speed and power consumption.

When a white-color LED as an illumination system for an image pickup element for the CMOS image-pickup element, the artificial retina LSI and threshold value modulation type image sensor (VMIS) is used, an yellow correction filter may be interposed before the image pickup element or the white LED (the correction filter is indicated by a reference numeral 50 in FIG. 8B). Thus, blue color having higher light emitting strength on light emitting spectrum of the white LED can be corrected. As a result, the light incident on the image pickup element has uniform color distribution so that an image of living body image can be reproduced with more natural colors, which is an excellent effect.

Third variation is a color image sensor for obtaining color signals of RGB in one pixel. In the color image sensor, three photo-detector (light receiving layer) is located in the depth (thickness) direction within silicon, and a characteristic that a light absorbing layer depends on the light wave length in the silicon is used. Thus, double resolution from a conventional image sensor can be achieved. This achieves advantages of a 3-CCD or a 3-shot camera by using a general single plate sensor.

Especially, this technology is implemented by the CMOS image sensor, such that it can be produced in low price, which is almost the same as the conventional type.

A method for reading out color signals of the color image sensor is the Variable Pixel Size (VPS) method, whereby several pixels of data are read out together. Thus, there is an advantage that the pixel size can be changed. Furthermore, there is an advantage that fast reading can be achieved, which is needed for higher sensitivity for photographing a still image and a video shooting (moving image shooting).

The structure prevents false colors, eliminating a need for a low pass filter as a result. Therefore, the color image sensor according to this method is suitable for capsule-type medical device needing to be compact and needing low power consumption. It is also suitable for the general type of videoscope.

In these days, a radio technology using pulses through broad bands has been developed. By using the technology, radio waves can be diffused to the broad band. Then, the radio transmission power can be close to the noise level. Therefore, this technology can be used together with the conventional narrow band communication.

In addition, since, unlike the narrow band communication, there is no carrier frequencies, signals can be analyzed directly. For example, by measuring an arrival time, distance information can be extracted with high precision. The distance information with high precision improves the precision of the position information.

Recently, as a typical pulse radio, an ultra wideband (UWB) technology is announced and is commercially available. If the UWB technology is incorporated into a radio communication device for a capsule-type medical device, a frequency having long wavelength can be used, which is easily transparent to a human body, for example. As the transparency to the human body is increased, the required amount of output power is more decreased. In addition, power consumption for radio communication device can be suppressed. Position information with high precision can be also obtained.

Second Embodiment

Figure 9:
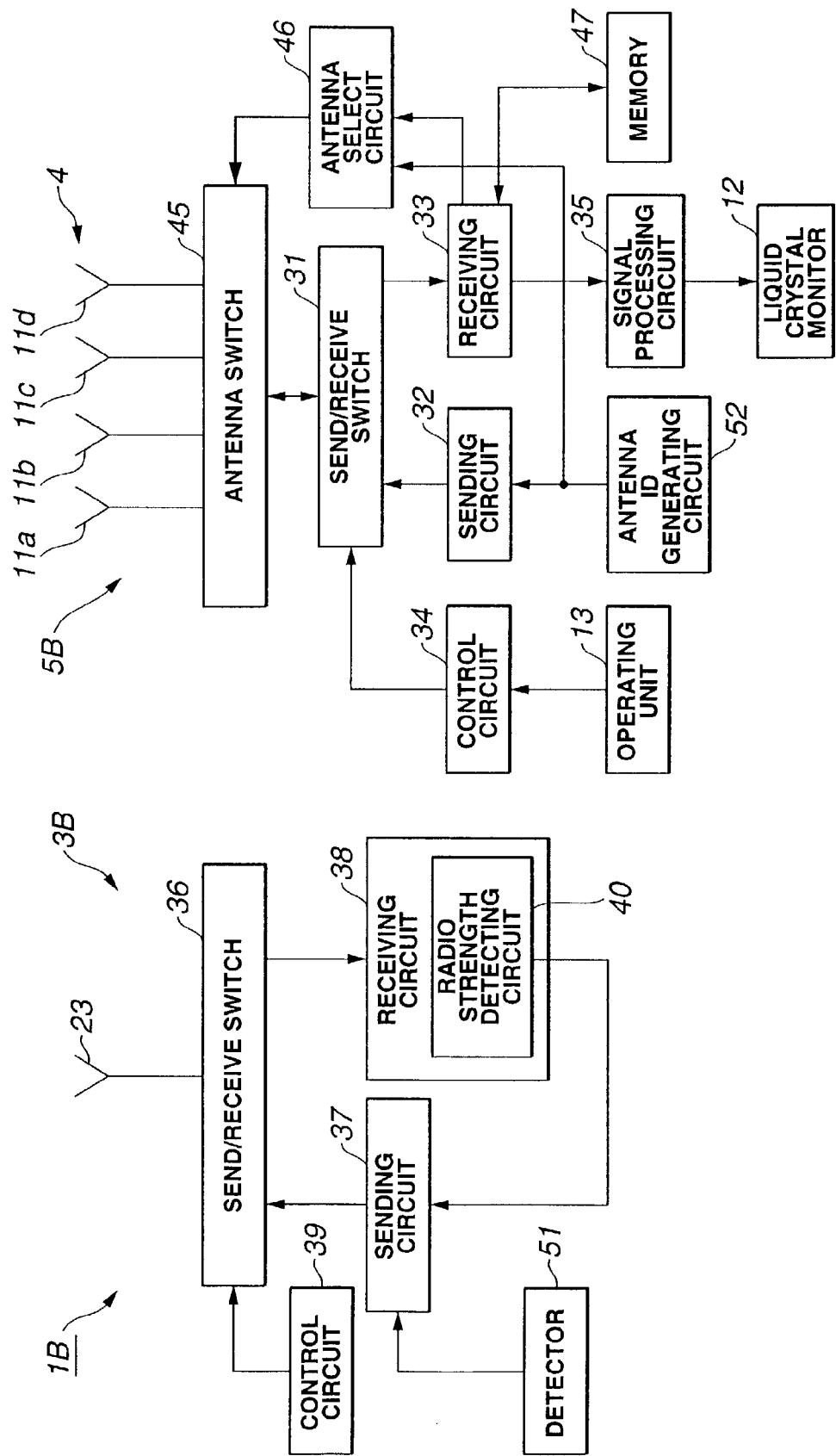
FIGS. 9 and 10 relate to a second embodiment of the present invention.

A second embodiment of the present invention will be described with reference to FIG. 9. FIG. 9 shows the configuration of a main portion of a capsule-type medical device 1B according to the second embodiment.

The capsule-type medical device 1B includes a capsule body 3B having a detector 51 such as a pH sensor for obtaining living body information and an external unit 5B for receiving and storing living body information from the capsule body 3B.

The capsule body 3B in the capsule endoscope 3 in FIG. 2 includes a detector 51 such as pH sensor instead of an illumination and image pickup means. Further, the external unit 5B has a function for storing information of the detector 51.

As shown in FIG. 9, the external unit 5B further includes an antenna ID generating circuit 52 in the configuration in FIG. 4. In other words, according to this embodiment, unique antennas are assigned to multiple antennas 11a to 11d, respectively. Thus, when transmission is performed from an antenna 11i, the antenna ID generated by the ID generating circuit 52 is modulated in digital in the sending circuit 32. Also, the antenna ID is sent to the antenna select circuit 46. The antenna select circuit 46 sets switching of the antenna switch 45 such that an antenna 11i corresponding to the antenna ID is selected. Then, the antenna ID is transmitted by radio waves.

The signal processing circuit 35 in FIG. 9 performs signal processing on signals detected in the detector 51 and causing the liquid crystal monitor 12 to display living body information such as pH values. Furthermore, the signal processing circuit 35 sends the living body information to a hard disk or a flash memory for storage.

The capsule body 3B in FIG. 4 includes the detector 51 instead of the image pickup device 43 and signals detected by the detector 51 are sent to the sending circuit 37.

When the capsule body 3B sends radio wave strength data detected by the radio wave strength detecting circuit 40 based on signals received by the receiving circuit 38 to the external unit 5B, respective antenna ID, which is received by the receiving circuit 38, is added to the beginning or ending portion of the radio wave strength data for transmission. Then, the external unit 5B side can identify an antenna corresponding to the radio wave strength data based on the antenna ID at the beginning or ending portion of the radio wave strength data. The other configuration is the same as that of the first embodiment.

In this embodiment, unique antenna IDs are assigned to multiple antennas 11a to 11d, respectively. Thus, when signals are sent via the antennas 11a to 11d, the transmission order can be changed. In addition, only specific antenna can be selected for signal receiving and sending.

For example, when the capsule body 3B moves within a body cavity, and when the antenna suitable for receiving maximum radio wave strength varies from 11a, 11b, to 11c, only a part of antennas, more specifically, only antennas 11b to 11d or antennas 11c to 11d can be used for sending signals, rather than using all of antennas 11a to 11d. Thus, an antenna suitable for receiving the maximum radio wave strength for the capsule body 3B can be detected.

In this case, since antenna IDs are assigned to antennas, it can be clearly detected which antenna is actually used for transmitting radio wave strength data from the capsule body 3B.

According to this embodiment, the multiple antennas 11a to 11d may be selected and be used more efficiently. The other advantages are almost the same as those of the first embodiment.

Figure 10:
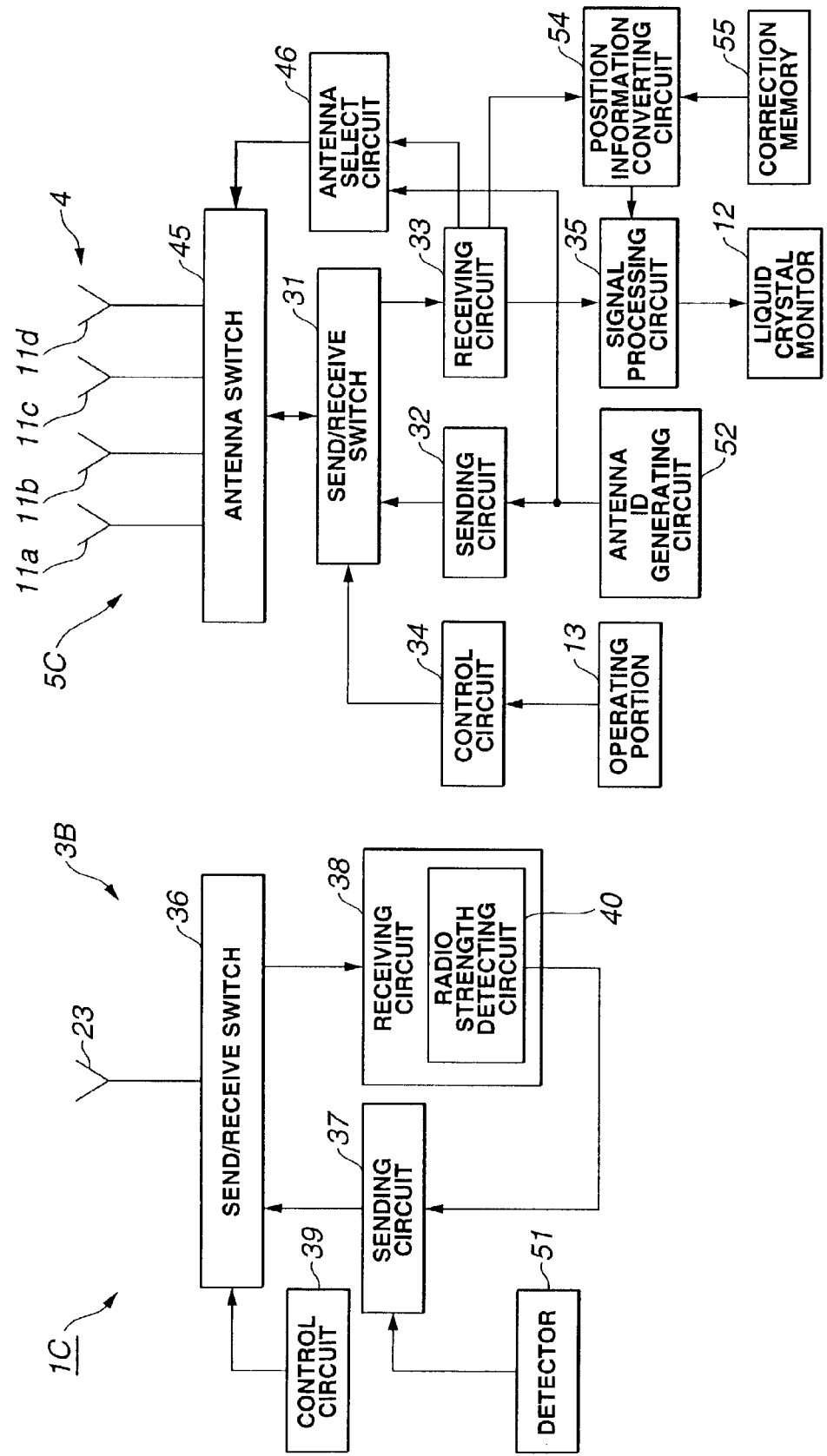

FIG. 10 shows the configuration of a main portion of an electric system for the capsule body 3B and the external unit 5C in the capsule-type medical device IC in the variation example.

In this variation example, the external unit 5B in FIG. 9 has a function for receiving radio wave strength data and for detecting position information, as described in the first embodiment.

In other words, radio wave strength data received by the receiving circuit 34 is sent to a position information converting circuit 54. The position information converting circuit 54 converts the radio wave strength data to position information. The calculated position information is sent from the position information converting circuit 54 to the signal processing circuit 35 and is used for displaying living body information on the liquid crystal monitor 12, for example.

In the variation example, there is provided a correction memory 55 for correcting a gain error in antennas 11a to 11d, loss components due to cables connected to the antennas 11a to 11d, and so on. Thus, the position information converting circuit 54 can calculate position information with high precision.

In this variation example, unique antenna IDs are assigned to the multiple antennas 11a to 11d, like those in FIG. 9. Radio wave strength data for only a specific antenna 11i can be obtained as necessary.

According to this variation example, position information can be obtained, which can be effectively used for diagnosis, in addition to the advantages of the second embodiment.

Third Embodiment

Figure 11:
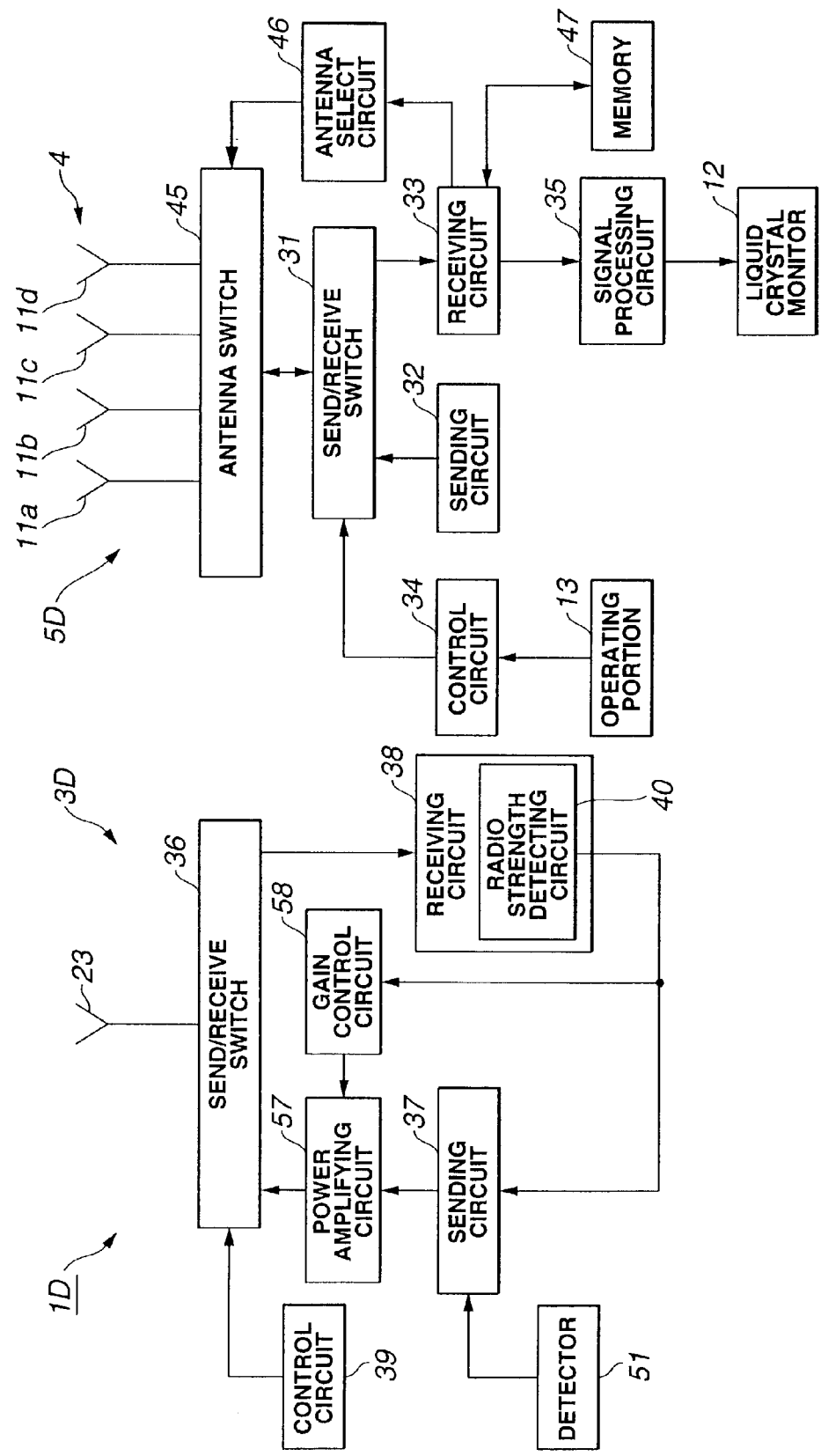

Next, a third embodiment of the present invention will be described with reference to FIG. 11. FIG. 11 shows the configuration of a main portion of a capsule-type medical device ID of the third embodiment.

An external unit 5D included in the capsule-type medical device ID shown in FIG. 11 has the same structure of that of the external unit 5 in FIG. 4. A capsule body 3D has basically the same configuration as that of the capsule endoscope 3 in FIG. 3.

In other words, the capsule body 3D has the configuration having a power amplifying circuit 57 for performing power amplification between the sending circuit 37 and the send/receive switch 36 and a gain control circuit 58 for controlling gain for power amplification by the power amplifying circuit 57 in addition to the configuration of the capsule body 3B in FIG. 9.

In this embodiment, gain for power amplification by the power amplifying circuit 57 is controlled through the gain control circuit 58 based on the output from the radio wave strength detecting circuit 40. Then, the gain control circuit 58 controls so as to set the transmission power, which allows the external unit 5D to receive signals properly.

According to a communication method used in the conventional example, communication is performed from the capsule body 3D to the external unit 5D in a single direction. In this case, when communication quality is the most important matter, the gain for the power amplifying circuit 55 within the capsule body 3D is set at a higher value. As a result, the power consumption in the capsule body 3D is increased.

On the other hand, when the power consumption is suppressed in order to avoid larger power consumption, it is not clearly realized whether or not the state that signals can be received surely is kept, making the maintenance of the communication quality difficult as a result.

Accordingly, in this embodiment, when living body information is sent from the external unit 5D based on the radio wave strength data, an antenna 11i, which can receive signals with the highest radio wave strength, can be selected for receiving (in the broad sense, for receiving and for sending) signals among the multiple antennas 11a to 11d in the external unit 5D. Further, the power amplifying circuit 57 and the gain control circuit 58, which can vary electricity gains, are provided. Thus, the transmission power from the capsule boy 3D to the external unit 5D is reduced to the level where signals can be received by using the antenna 11i, with the highest radio wave strength. As a result, the power consumption in the capsule body 3D may be suppressed.

In other words, according to this embodiment, by keeping the state where a predetermined communication quality can be maintained, and by keeping the lowest transmission power, which can achieve the state, wasteful consumption of electric energy in the capsule body 3D can be suppressed. As a result, the operationable time by using a built-in battery can be increased.

Figure 12:
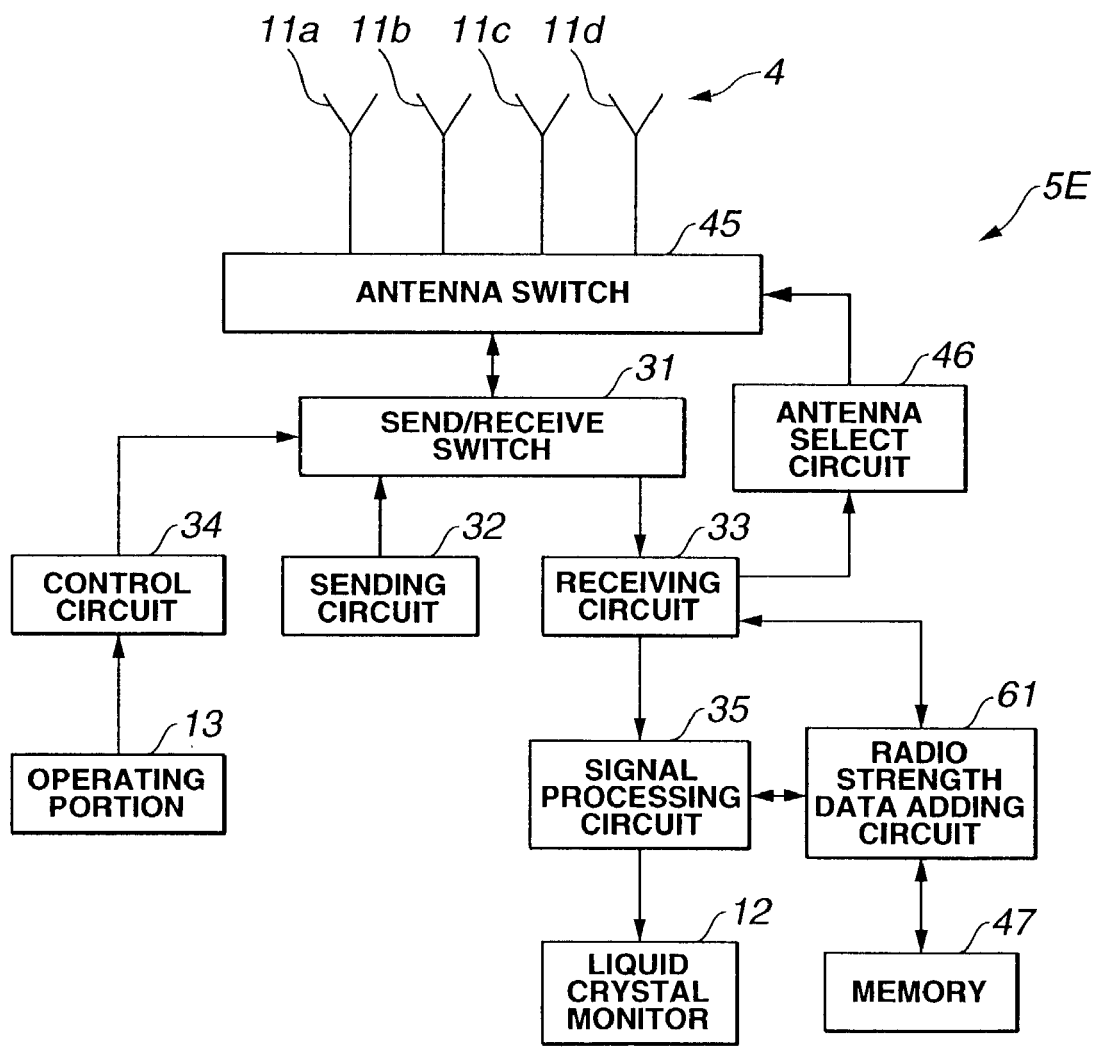

FIG. 12 shows the configuration of an external unit 5E of a first variation example. The external unit 5E includes a radio wave strength data adding circuit 61 for adding radio wave strength data in the external unit 5D in FIG. 11. Data received by the receiving circuit 33 is stored in the memory 47 via the radio wave strength data adding circuit 61. The data received by the receiving circuit 33 may be temporally stored in the memory 47, and radio wave strength data may be added by the radio wave strength data adding circuit 61 based on the stored data.

Figure 13:
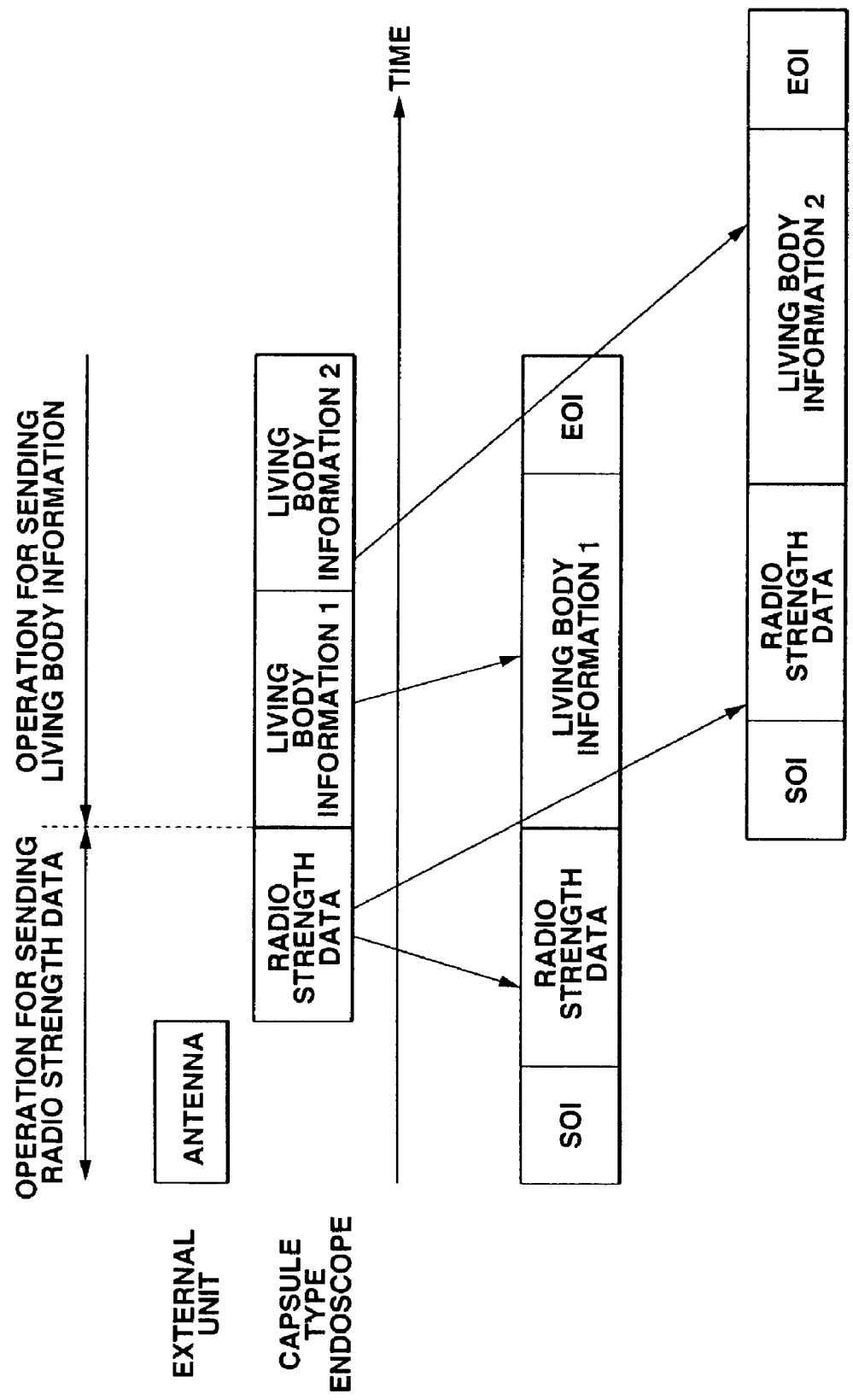

FIG. 13 shows an explanatory diagram of an operation for signal transmission between the capsule body 3D and the external unit 5E in this case.

As shown in FIG. 13 (as described in FIG. 5 or FIG. 6), the external unit 5E sends signals at sure strength by switching antennas during the period for the operation for sending radio wave strength. The capsule body 3D receives the signals and creates radio wave strength data by using the radio wave strength detecting circuit 40. Then, the external unit 5E sends the radio wave strength data and sets an antenna 11*i* by which signals can be received with the highest radio wave strength.

Then, the processing goes to an operation for sending living body information and the capsule body 3D sends living body information 1, living body information 2, and so on.

The external unit 5E receives the living body information 1, living body information 2 and so on through the receiving circuit 33 and adds radio wave strength data to those information by using the radio wave strength data adding circuit 61. Then, a file for a signal format is created as shown in FIG. 13.

In other words, a file having a start mark SOI, followed by radio wave strength data, the living body information 1 or the living body information 2 and a file end mark EOI. In this way, the file (for living body information I) is created by adding radio wave strength data obtained immediately before the living body information I (I=1, 2, or the like). Then, the signal processing circuit 35 calculates position information from the radio wave strength data. The calculated position data can be used effectively such as being displayed together with the living body information I.

Figure 14:
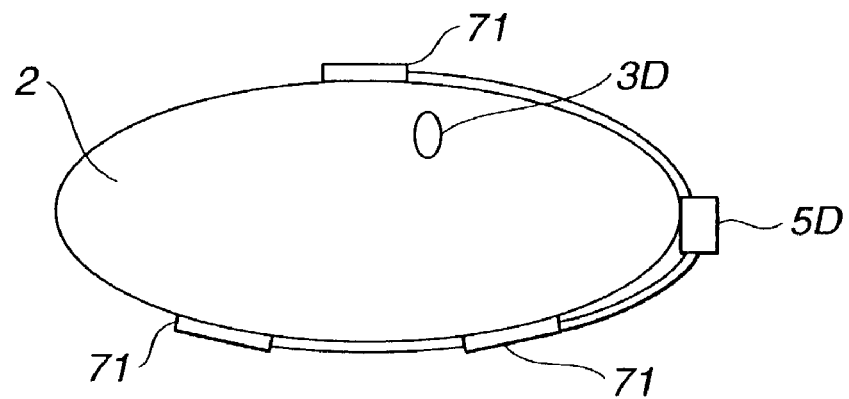

FIG. 14 schematically shows a second variation example. It is an object of this variation example to provide a capsule-type medical device, which is strung against external noise and interference radio waves (or interfering radio waves). In the related technology, external noise and the like are not fully considered. Thus, it is the object to provide a capsule-type medical device which overcomes the above problem and has good communication quality between the capsule-type endoscope and the external unit.

In this variation example, as shown in FIG. 14, multiple antennas 71 having a single orientation as an antenna unit on the external side, which is used externally, are located such that they are directed to the inside of a body.

The antenna 71 with higher orientation used in this case may be a patch antenna used for a GPS. Since the capsule body 3D is kept within a body, it can be surely within the range of the multiple antennas of the external unit 5D. Therefore, the use of the antennas 71 with high orientation on the external unit 5D side increases the strength against external interference radio waves.

Figure 15:
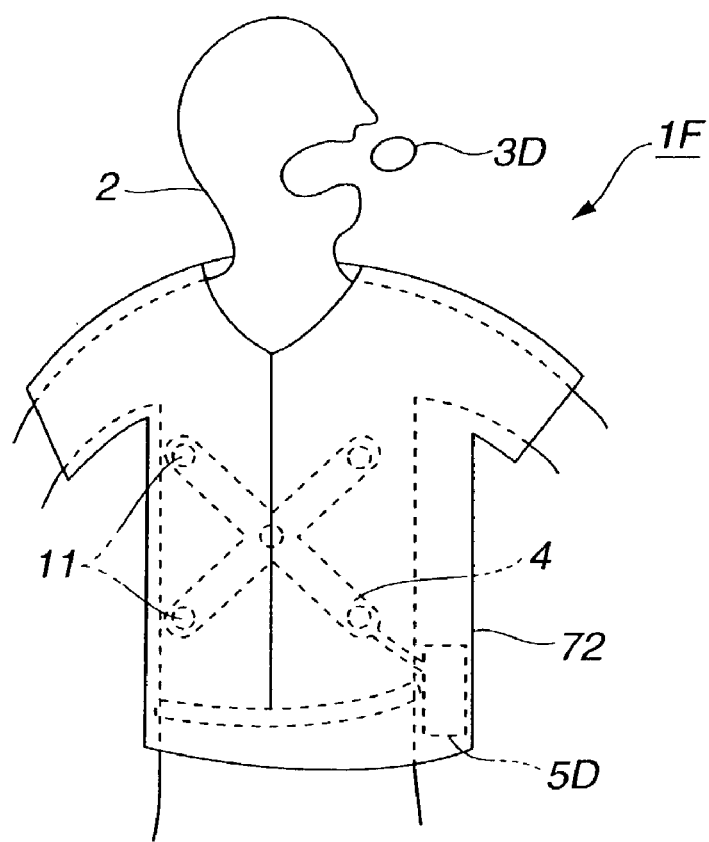

FIG. 15 shows an example where a capsule-type medical device 1F according to a third variation example is used. The object of this variation example is the same as that of the second variation example. In this variation example, the capsule-type medical device 1D according to the third embodiment is arranged such that the antenna unit 4 and the external unit 5 are covered by a cloth formed with electromagnetic shield fibers, more specifically, by a shield jacket 72, as shown in FIG. 15. The electromagnetic shield fibers may be metal fibers, metal chemical fibers and copper sulfide contained fibers.

Figure 16:
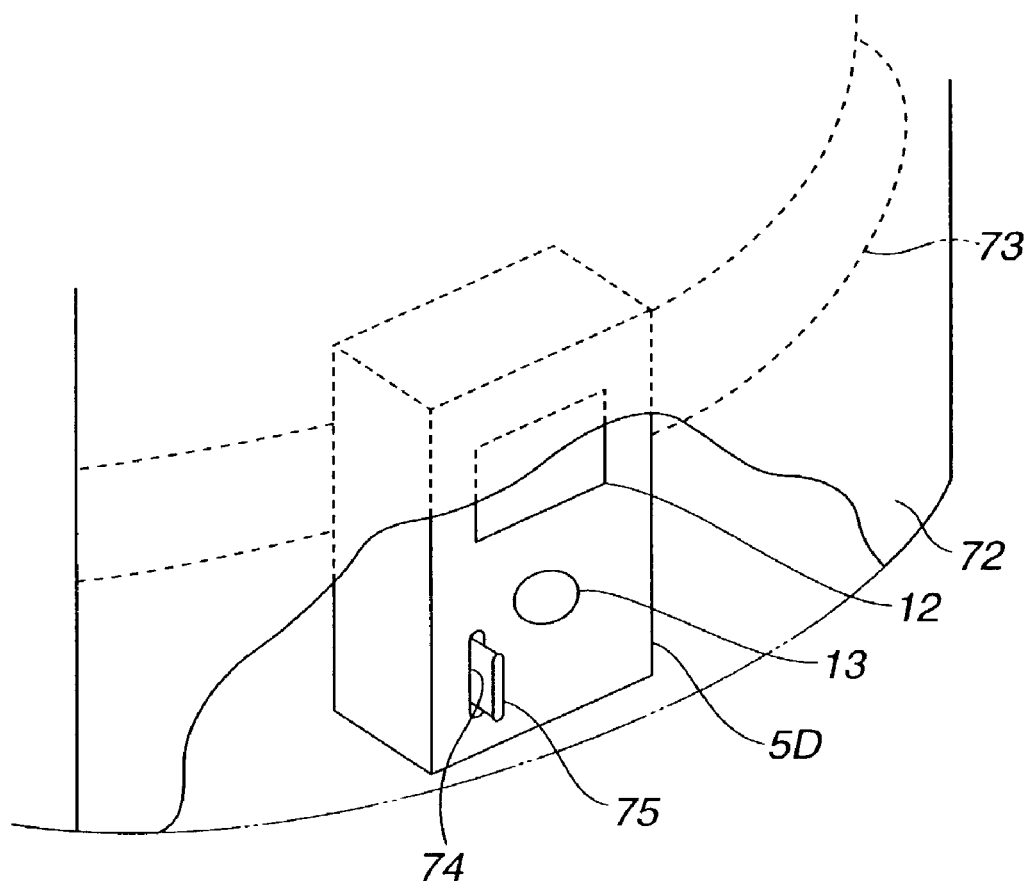

When the shield jacket 72 is worn, a key 75 provided in the shield jacket 72 can be inserted removably to a keyhole 74 in the external unit 5, which is attached to a belt 73 removably as shown in FIG. 16.

Figure 17A:
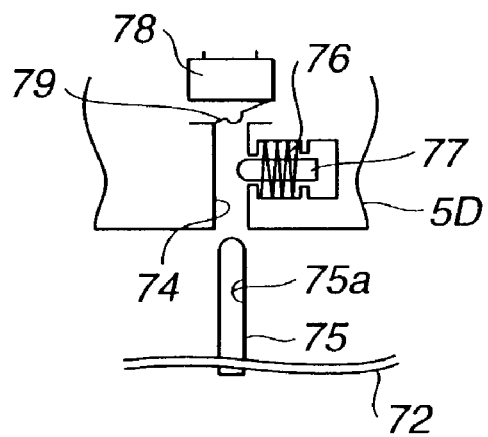
FIG. 17A is a diagram showing the configuration of a keyhole provided in the external unit side, from which a key of the shield jacket side is removable.
Figure 17B:
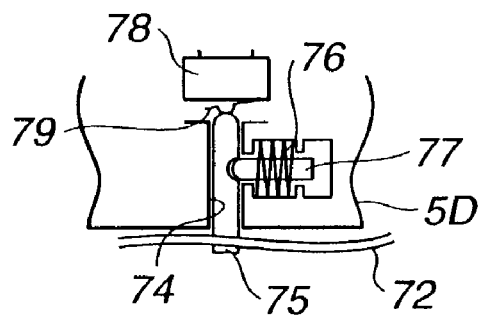

As shown in FIG. 17A, in the keyhole 74 in the external unit 5D, a key holding member 77 energized by a spring 76 projects from a side crossing the hole direction of the keyhole 74 into the center side of the keyhole 74. When the key 75 is inserted to the keyhole 74, the end of the key holding member 77 fits to a recess portion 75*a* provided in the middle of the key 75, which keeps the key 75 attached, as shown in FIG. 17B.

A switch lever 79 for a microswitch 78 is located in the depth side of the keyhole 74 such that it faces with the keyhole 74. When the key 75 is inserted to the keyhole 74, the switch lever 79 is pressed by the pointed end of the key 75. Then, the switch lever 79 is turned from the OFF (FIG. 17A) to ON (FIG. 17B).

The switching ON turns ON the power supply switch of the external unit 5D. Then, power supply is supplied to the inside circuits and so on, which brings to an operation state.

In this configuration, when a patient 2 uses the cloth woven from electromagnetic shield fibers such that data can be protected from external noises and/or interference radio waves. Thus, a function for checking whether or not the patient 2 wears the cloth is provided in the external unit 5D, and it is arranged that the examination can be performed by the capsule-type medical device IF only when the cloth is worn.

In this case, since the capsule body 3D and the external unit 5D are covered by the cloth woven from electromagnetic shield fibers, signals can be exchanged between the capsule body 3D and the external unit 5D with less influences of external radio waves.

Fourth Embodiment

Figure 18:
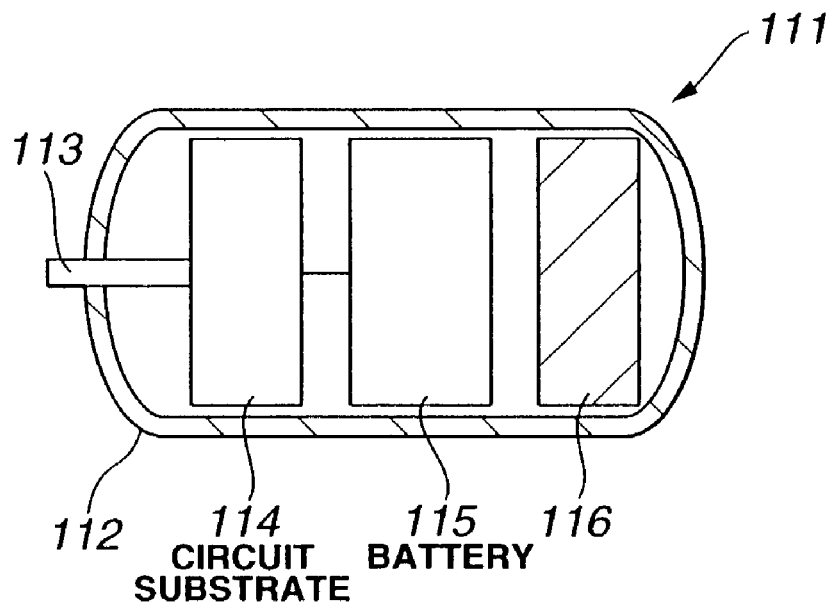
FIGS. 18 to 21 relate to a fourth embodiment of the present invention.

A fourth embodiment of the present invention will be described with reference to FIG. 18. FIG. 18 shows a capsule-type medical device 111 according to the fourth embodiment of the present invention.

The capsule-type medical device 111 includes a capsule body 112 having a watertight structure having a cylinder portion and round covers covering the both ends. For example, a detecting portion for a pH sensor 113 for detecting pH within a body cavity may project (expose) into one of the end portion side.

When the detecting portion of the pH sensor 113 projects from a hole portion of the capsule body 112, it is fixed with a highly watertight bond in order to achieve the watertight structure inside.

The rear end side of the pH sensor 113 is connected to a circuit substrate 114 including functions for performing a pH detection processing provided within the capsule body 112, for storing detected pH data, for communicating with the outside and so on. The circuit substrate 114 is connected to a battery 115 for supplying power source for operating the circuit substrate 114. The battery 115 may be highly efficient fuel cell made of silver oxide or with a high degree of shape flexibility.

In this embodiment, a permanent magnet (or a ferromagnet strongly acting on magnetism such as iron) 116 is accommodated near the other end portion opposite to the pH sensor 113 within the capsule body 112.

When the capsule-type medical device 111 stops at, for example, a narrowing portion, it can be collected by using a collecting tool having a long and narrow tube shape, such as an ileus tube, and accommodating the permanent magnetic. The permanent magnet or the ferromagnet 116 may be accommodated within the capsule-type endoscope 3 shown in FIG. 2.

In this embodiment, the pH sensor 113 for detecting pH is used as medical examination means (detecting unit). However, a temperature sensor, a pressure sensor, a light sensor or a blood sensor (more specifically, sensor for detecting hemoglobin) may be adopted. The other sending and receiving methods between the capsule-type medical device 111 and the external unit 5 are the same as those of the second embodiment.

In this way, information such as a chemical amount of a living body secretion (pH value), a temperature of each organ, a pressure from inside of a tube cavity acting on the external surface of the capsule when the capsule passes, the brightness within the living body, an amount of hemoglobin in each organ (the presence of bleeding) is obtained by using the sensor portion (detecting unit). Then, the obtained data is once stored in a memory within the capsule, not shown. After that, the data is sent to a receiving unit located outside of the body through a communication unit. By comparing the data obtained by the receiving unit and a reference value, the presence of abnormality such as illness and bleeding can be determined by doctor or a medical attendant such as a co-medical person.

Especially, by using the capsule-type medical device, the pH value or an amount of hemoglobin within the alimentary canal of a living body can be measured for diagnoses of digestive organ diseases and physiological analysis without giving pain to a subject, which is a big advantage. Efficient examination can be performed by using multiple kinds of sensors suitable for purposes. Since sending and receiving data are performed efficiently, there is an advantage that measurement for many hours can be performed by keeping the battery lifetime longer.

Figure 19:
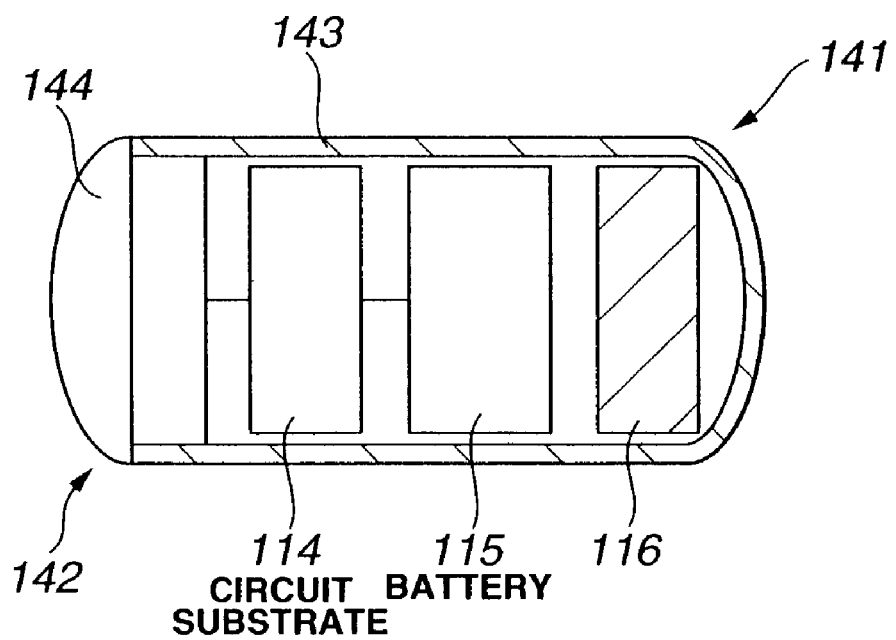

While the capsule-type medical device 111 including each different kind of sensor is described in FIG. 18, a capsule-type medical device 141 including an ultrasonic wave probe 142 may be used as shown in FIG. 19 instead of the sensor.

In the capsule-type medical device 141, a sound lens 144 provided on the front surface of the ultrasonic probe 142 is exposed to the external surface of the capsule body 143. The sound lens 144 is fixed in a capsule body 143 watertightly by using a bond, for example, and the inside of the capsule has a watertight structure.

A ultrasonic wave sending and receiving circuits and a circuit substrate 114 performing processing for creating a ultrasonic wave tomogram image from signals are arranged inside of the capsule at the back side of the ultrasonic wave probe 142. The circuit substrate 114 is driven by a power supply from the battery 115. The permanent magnet 116 is accommodated at the back end side.

In the capsule-type medical device 141, an ultrasonic wave tomogram image of the inside of a body cavity is created by the ultrasonic wave sending and receiving circuits formed by the circuit substrate 114. Then, the obtained data is sent to the receiving unit outside of the body, like the case in FIG. 18. Thus, the presence of abnormalities in the depth direction of the depth portion within the body cavity, such as the small intestine, can be diagnosed for many hours.

An optical observing unit (image pickup means) may be further provided. By using the configuration, the surface and the depth portion within the body cavity can be diagnosed at the same time.

Figure 20:
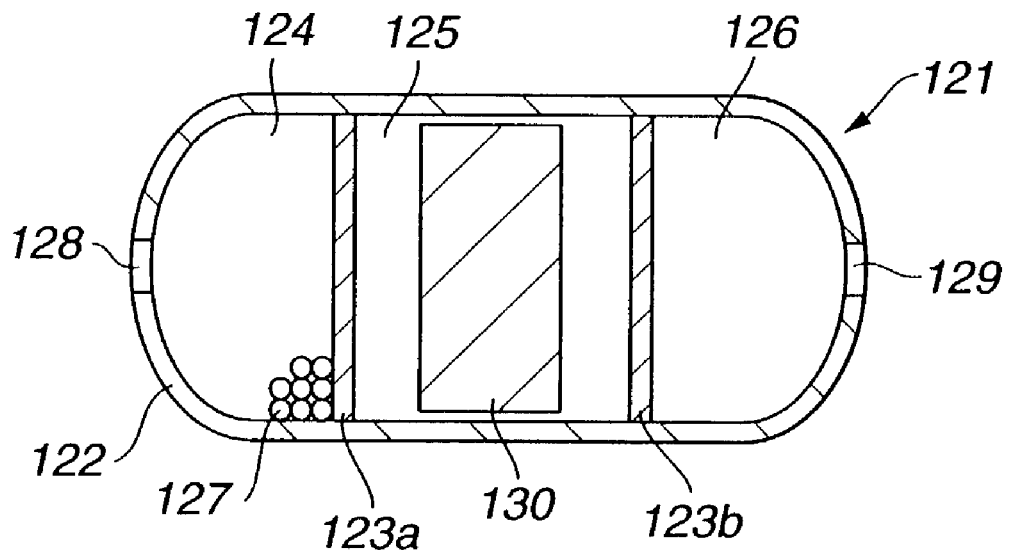

FIG. 20 shows a capsule-type medical device 121 in the second variation example.

The capsule type-medical device 121 includes a capsule body 122 formed by a cylinder and round covers covering the both ends. The capsule body 122 is partitioned by partitioning members 123a and 123b at two positions in the length direction, which has three accommodating portions of a medicine accommodating portion 124, a permanent magnet/magnet accommodating portion 125 and a body fluid sucking portion 126.

A medicine 127 for treatment is accommodated in the medicine accommodating portion 124. A dosing opening 128 is provided as an opening portion for releasing the accommodated medicine 127 to the outside.

A body fluid sucking point 129 for sucking body fluid from the outside of the capsule body 122 is also provided at the body fluid sucking opening portion 126, which is provided at the opposite side of the medicine accommodating portion 124.

A permanent magnet or magnet 130 is accommodated by the permanent magnet/magnet accommodating portion 125.

Soluble films 128a and 129a containing a gelatin, which is digested by gastric juice, and a fatty acid film, which is digested by intestinal juice, are provided at the dosing opening 128 and the body fluid sucking opening 129.

When the capsule-type medical device 121 reaches a target part, a control signal is sent from the external unit 5B. The control signal is received by the capsule-type medical device 121. Then, the soluble film 128a and so on is digested in order to dose the medicine 127 for treatment or to suck body fluids. Furthermore, a release signal is sent from the external unit 5B. Then, the capsule-type medical device 121 receives the release signal in order to control the release.

According to this variation example, treatment and/or examination can be performed at a target part by, for example, sucking body fluids.

Figure 21:
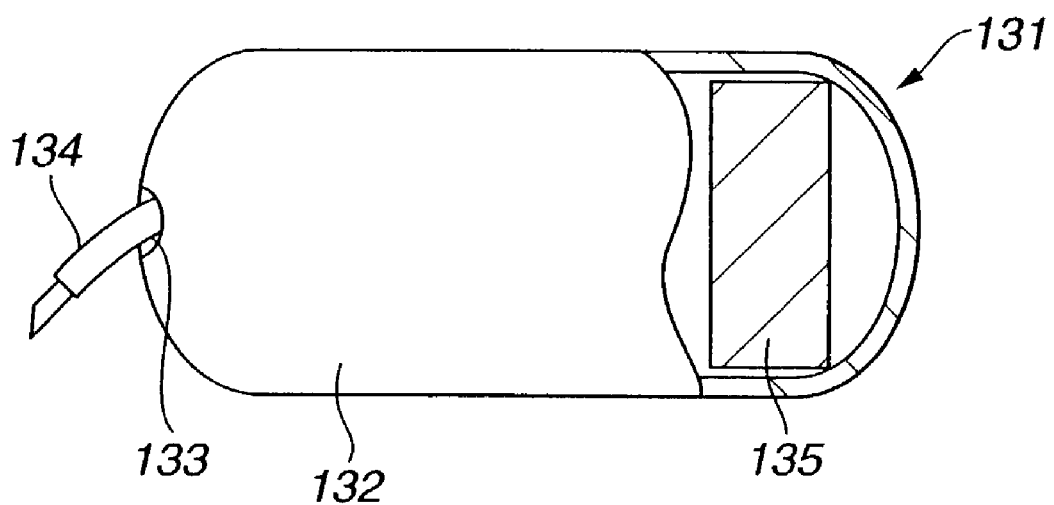

FIG. 21 shows a capsule-type medical device 131 according to the third variation example.

The capsule-type medical device 131 includes a capsule body 132 formed by a cylinder and round covers covering both of the ends. An opening 133 is provided at one end portion, which allows a medicine infusing injection needle 134 to project and to retract freely. Drive means for projecting and retracting the medicine infusing injection needle 134 and a control unit for the drive unit are located within the capsule body 132. A control signal is sent from the external unit 5B. The capsule type medical device 131 receives the control signal such that the medicine infusing injection needle 134 can project and retract to infuse medicine.

A permanent magnet/magnet 135 is accommodated near the end portion opposite to the opening 133 within the capsule body 132.

After realizing a bleeding part by using a blood sensor or observation means, an instruction for operation is given to a treatment tool such as a hemostatic infusing needle accommodated within the capsule through communication from the outside of the body. Then, ethanol or powdered medicine, which is a hemostatic, is sprayed to stop bleeding.

According to this variation example, treatment such as stopping of bleeding can be performed with keeping the battery lifetime longer.

An embodiment constructed by combining the above embodiments partially also belongs to the present invention.

Also, having described the preferred embodiments of the invention referring to the accompanying drawings, it should be understood that the present invention is not limited to those precise embodiments, but that various changes and modifications thereof could be made by one skilled in the art without departing from the spirit or scope of the invention as defined in the appended claims.

What is claimed is:

1. A capsule-type medical device, comprising:
   a capsule inserted into a living body, having a living body information detecting device for obtaining living body information;
   an external unit located outside of the living body;
   a first sending and receiving circuit provided in the external unit for signal sending and receiving;
   a first antenna connected to the first sending and receiving circuit;
   a second sending and receiving circuit located in the capsule for signal sending and receiving;
   a second antenna connected to the second sending and receiving circuit;
   a radio wave strength detecting circuit for detecting radio wave strength when a signal sent from the first sending and receiving circuit side via the first antenna is received by the second sending and receiving circuit via the second antenna; and
   a transmission power control circuit for controlling a gain of transmission power by the second sending and receiving circuit based on an output detected by the radio wave strength detecting circuit.

2. The capsule-type medical device according to claim 1, wherein the living body information detecting device has an image pickup device including an objective lens and an image pickup element.

3. The capsule-type medical device according to claim 2, wherein the image pickup element is a CMOS image-pickup element or a threshold value modulating type image sensor.

4. The capsule type medical device according to claim 2, wherein the image pickup device is a so-called artificial retina LSI, which is a system LSI having an image processing circuit added to the CMOS image-pickup element on one chip.

5. The capsule-type medical device according to claim 2, further comprising an illumination device using a white light emitting diode generating white illumination light.

6. The capsule-type medical device according to claim 5, further comprising a color correction filter for correcting a color having higher light emitting spectrum from a used white LED on the front surface of the image pickup element or on the front surface of the illumination device.

7. The capsule-type medical device according to claim 1, wherein the living body information detecting device is at least one of a pH sensor, a temperature sensor, a pressure sensor, a light sensor and a blood sensor.

8. The capsule-type medical device according to claim 1, wherein the living body information detecting device is an ultrasonic wave probe.

9. The capsule-type medical device according to claim 1, wherein the capsule has, in addition to the living body information detecting device, a operation control circuit for operating, in response to an instruction from the external unit, body fluids sucking for treatment or examination on a target part.

10. The capsule-type medical device according to claim 1, wherein the first antenna has a plurality of antennas.

11. The capsule-type medical device according to claim 1, wherein a member formed of magnet or ferromagnet is accommodated in the capsule.

12. The capsule-type medical device according to claim 10, further comprising a position information calculating circuit for calculating information on a position of the capsule by using the plurality of antennas.

13. The capsule-type medical device according to claim 10, wherein the plurality of antennas have a high orientation for ending and receiving radio waves toward the inside of a subject to be examined by the capsule.

14. The capsule-type medical device according to claim 10, wherein the capsule sends information on the radio wave strength, and the external unit selects an antenna to be actually used among the plurality of antennas based on the received information.

15. The capsule-type medical device according to claim 1, wherein the outer side of the first antenna is electromagnetically shielded.

16. A capsule-type medical device, comprising:
    a capsule inserted into a living body, having a living body information detecting device for obtaining living body information;
    an external unit located outside of the living body;
    a first sending and receiving circuit provided in the external unit for signal sending and receiving;
    a plurality of first antennas connected to the first sending and receiving circuit;
    a second sending and receiving circuit located in the capsule for signal sending and receiving;
    a second antenna connected to the second sending and receiving circuit;
    a radio wave strength detecting circuit for detecting radio wave strength when a signal sent from the first sending and receiving circuit side via the plurality of first antennas is received by the second sending and receiving circuit via the second antenna; and
    a transmission power control circuit for controlling a gain of transmission power by the second sending and receiving circuit based on an output detected by the radio wave strength detecting circuit,
    wherein the information on radio wave strength detected by the radio wave strength detecting circuit when the plurality of first antennas are used can be sent from the capsule side to the external unit side.

17. The capsule-type medical device according to claim 16, wherein the external unit receives radio wave strength information sent from the capsule side and, then, selects an antenna from the plurality of first antennas for actually receiving information set from the capsule side.

18. The capsule-type medical device according to claim 16, wherein information sent as radio waves from the plurality of first antennas includes ID codes for the first antennas, respectively.

19. The capsule-type medical device according to claim 16, wherein the capsule sends information on radio wave strength detected by the radio wave strength detecting circuit and living body information detected by the living body information detecting device.

20. The capsule-type medical device according to claim 19, wherein frequency for sending the information on radio wave strength, which is sent from the capsule, is less than the frequency for sending the living body information.

21. The capsule-type medical device according to claim 16, wherein the external unit has a correction circuit for correcting gains by the plurality of first antennas, a loss caused by a cable connected thereto, and so on.

22. The capsule-type medical device according to claim 16, wherein a gain of transmission power in the first sending and receiving circuit is controlled based on the information on radio wave strength.

23. The capsule-type medical device according to claim 16, wherein the external unit has a memory medium for storing living body information and so on, and the memory medium stores living body information and information on radio wave strength.

24. The capsule-type medical device according to claim 16, wherein the living body information detecting device has an image pickup device including an objective lens and an image pickup element.

25. The capsule-type medical device according to claim 24, the image pickup element is a CMOS image-pickup element or a threshold value modulating type image sensor.

26. The capsule type medical device according to claim 24, wherein the image pickup device is a so-called artificial retina LSI, which is a system LSI having an image processing circuit added to the CMOS image-pickup element on one chip.

27. The capsule-type medical device according to claim 24, further comprising an illumination device using a white light emitting diode generating white illumination light.

28. The capsule-type medical device according to claim 16, wherein the living body information detecting device is at least one of a pH sensor, a temperature sensor, a pressure sensor, a light sensor and a blood sensor.

29. The capsule-type medical device according to claim 16, wherein the living body information detecting device is an ultrasonic wave probe.

30. A capsule-type medical device, comprising:
a detecting device for detecting living body information; and
a capsule inserted into a living body, for modulating detected living body information and sends it by radio waves;
an external unit for demodulating radio waves sent from at least the capsule and for storing living body information in a memory;
wherein the external unit includes a plurality of first antennas, an antenna switching circuit for sequentially switching the plurality of first antennas, a first sending circuit and a first receiving circuit for sending and receiving signals to the capsule side, a first send/receive switching circuit for selecting either connection of the plurality of first antennas to the first sending circuit or to the first receiving circuit, and an antenna select circuit for selecting one of the plurality of first antennas, which is used for communicating the living body information with the first sending circuit,
wherein the capsule includes a second send/receive switching circuit connected to a second antenna provided in the capsule for selecting connection with either circuit of the second sending circuit or with the second receiving circuit for sending and receiving signals, a radio wave strength detecting circuit for detecting radio wave strength corresponding to respective first antennas, which are sequentially emitted from the plurality of first antennas to output it as radio wave strength data, and a transmission power control circuit for controlling a gain of transmission power by the second sending and receiving circuit based on an output detected by the radio wave strength detecting circuit, and
wherein a radio wave strength data operation for sending modulating the radio wave strength data in the second sending circuit and for sending it by radio waves is performed as upstream processing.

31. A capsule-type medical device, comprising a capsule inserted into a living body, having a detecting device for detecting living body information;
an external unit located outside of the living body for receiving living body information sent from the capsule by radio waves;
wherein the external unit has a first antenna, a first sending circuit and a first receiving circuit for sending and receiving signals, and a first send/receive switching circuit for selecting the first sending circuit or the first receiving circuit to be connected to the first antenna,
wherein the capsule has a second antenna, a second sending circuit and a second receiving circuit or sending and receiving signals, a second send/receive switching circuit for selecting the second sending circuit or the second receiving circuit to be connected to the second antenna, and a radio wave strength detecting circuit for detecting the strength of radio waves emitted from the first antenna and output it as radio wave strength data; and
wherein an operation by the second sending circuit is controlled based on the radio wave strength data.

32. The capsule-type medical device according to claim 31, wherein a gain of a signal sent from the second sending circuit is variably controlled based on the radio wave strength data.

33. A capsule-type medical device, comprising a capsule inserted into a living body, having a living body information detecting device for detecting living body information;
an external unit located outside of the living body for receiving living body information sent from the capsule by radio waves;
wherein the external unit has a plurality of first antennas, a first sending and a first receiving circuit for sending and receiving signals, an antenna switching circuit for sequentially switching the plurality of first antennas, and a first send/receive switching circuit for selecting the first sending circuit or the first receiving circuit to be connected to an antenna selected by the antenna switching circuit,
wherein the capsule includes a second antenna, a second sending circuit and a second receiving circuit for sending and receiving signals and a second send/receive switching circuit for selecting the second sending circuit or the second receiving circuit to be connected to the second antenna, a radio wave strength detecting circuit for detecting the strengths of radio waves, which is sequentially emitted from the plurality of first antennas, corresponding to the respective first antennas and for outputting it as radio wave strength data, and a transmission power control circuit for controlling a gain of transmission power by the second sending and receiving circuit based on an output detected by the radio wave strength detecting circuit, and
wherein the radio wave strength data is modulated in the second sending circuit and is sent by radio waves.

34. The capsule-type medical device according to claim 33, further comprising a position information converting circuit for converting the radio wave strength data to position information.

35. The capsule type medical device according to claim 34, wherein information sent as radio waves from the plurality of first antennas includes ID codes to be used for identifying the respective first antennas.

36. The capsule-type medical device according to claim 33, wherein the living body information detecting device is at least one of a pH sensor, a temperature sensor, a pressure sensor, a light sensor and a blood sensor.

37. A capsule-type medical device, comprising:
a capsule inserted into a living body, having a detecting device for detecting living body information and a first sending circuit for modulating the detected living body information and for sending it by radio waves;
an external unit having a first receiving circuit for demodulating radio waves sent from the capsule to obtain living body information and a memory for storing the living body information; and
a determination device for determining whether or not a subject wears a cloth made from electromagnetic shield fibers including the external unit during examination.

38. A capsule-type medical device, comprising;
a capsule inserted into a living body, having a detecting device for detecting living body information and a sending circuit for modulating the detected living body information and for sending it by radio waves; and
an external unit having a receiving circuit for demodulating radio waves sent from the capsule to obtain living body information and a memory for storing the demodulating living body information,
wherein the external unit is located such that a plurality of antennas having single direction orientation directs toward the inside of the body.

39. The capsule-type medical device according to claim 2, wherein the image pickup element is a color image sensor having three photo-detector (light-receiving layer) within silicon located in the depth (thickness direction), for obtaining respective color signals of RGB in one pixel.

40. The capsule-type medical device according to claim 39, wherein the color image sensor is a CMOS image sensor.

41. The capsule-type medical device according to claim 39, wherein a method for reading out color signals by the color image sensor is a variable pixel size (VPS) method, whereby several pixels of data is read out once.

42. A capsule-type medical device, comprising:
a capsule inserted into a living body, having a living body detecting device for obtaining living body information;
an external unit located outside of the living body; and
radio communication devices provided in the capsule and the external units, which uses communication means through pulses, the communication device provided in the capsule being configured to transmit the living body information to the external units, the transmission power of the communication device provided in the capsule being variable dependant on signal strength data determined from signals received from the communication device provided in the external units.

43. The capsule-type medical device according to claim 42, wherein the communication means is an ultra wideband (UWB) method.

* * * * *